US012399537B2

(12) United States Patent
Jeong et al.

(10) Patent No.: US 12,399,537 B2
(45) Date of Patent: Aug. 26, 2025

(54) ELECTRONIC DEVICE FOR DETECTING MOISTURE

(71) Applicant: Samsung Electronics Co., Ltd., Suwon-si (KR)

(72) Inventors: Daeung Jeong, Suwon-si (KR); Suho Lee, Suwon-si (KR); Shinhee Cho, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 321 days.

(21) Appl. No.: 17/884,990

(22) Filed: Aug. 10, 2022

(65) Prior Publication Data

US 2023/0161384 A1    May 25, 2023

Related U.S. Application Data

(63) Continuation of application No. PCT/KR2022/011583, filed on Aug. 4, 2022.

(30) Foreign Application Priority Data

Nov. 22, 2021 (KR) .................. 10-2021-0161385
Dec. 10, 2021 (KR) .................. 10-2021-0176613

(51) Int. Cl.
  *G06F 1/16* (2006.01)
  *G06F 3/01* (2006.01)
  *G06F 3/041* (2006.01)

(52) U.S. Cl.
  CPC ............ *G06F 1/1656* (2013.01); *G06F 1/163* (2013.01); *G06F 3/016* (2013.01); *G06F 3/04164* (2019.05)

(58) Field of Classification Search
  None
  See application file for complete search history.

(56) References Cited

U.S. PATENT DOCUMENTS 8,698,769 B2    4/2014  Coulson et al.
9,298,327 B2    3/2016  Wenzel
(Continued)

FOREIGN PATENT DOCUMENTS

CN    110367952 A    10/2019
CN    112731833 A    4/2021
(Continued)

OTHER PUBLICATIONS

International Search Report dated Nov. 18, 2022, issued in an International Patent Application No. PCT/KR2022/011583.
(Continued)

*Primary Examiner* — Imani N Hayman
*Assistant Examiner* — Rashen E Morrison
(74) *Attorney, Agent, or Firm* — Jefferson IP Law, LLP

(57) ABSTRACT

An electronic device is provided. The electronic device includes a housing including a first surface, a second surface and a conductive frame disposed between the first surface and the second surface and including a through-hole, a first electrode is movable within the through-hole, a part of the first electrode protruding to outside of the conductive frame, a second electrode disposed on the second surface, and at least one processor. The at least one processor is configured to identify whether the first electrode is electrically disconnected to the conductive frame, obtain an information about the user' body through the first electrode and the second electrode, and refrain from obtaining the information based on identifying the first electrode is electrically connected to the conductive frame.

20 Claims, 11 Drawing Sheets

(56) References Cited

U.S. PATENT DOCUMENTS

| | | | |
|---|---|---|---|
| 9,823,286 B2 | 11/2017 | Connell et al. | |
| 10,610,157 B2* | 4/2020 | Pandya | G04G 21/08 |
| 10,627,783 B2* | 4/2020 | Rothkopf | G06F 3/016 |
| 11,073,950 B1 | 7/2021 | Lee et al. | |
| 11,150,766 B2 | 10/2021 | Hong et al. | |
| 11,857,298 B1* | 1/2024 | Allec | G06F 1/163 |
| 2019/0101870 A1* | 4/2019 | Pandya | A61B 5/339 |
| 2019/0133487 A1 | 5/2019 | Jung et al. | |
| 2019/0320981 A1 | 10/2019 | Kodama et al. | |
| 2021/0257086 A1 | 8/2021 | Kang et al. | |
| 2021/0275102 A1 | 9/2021 | Cho et al. | |
| 2022/0117533 A1 | 4/2022 | Mattila et al. | |
| 2023/0161384 A1* | 5/2023 | Jeong | A61B 5/28 361/679.26 |
| 2023/0221816 A1 | 7/2023 | Rosenberg et al. | |

FOREIGN PATENT DOCUMENTS

| | | |
|---|---|---|
| CN | 112762701 A | 5/2021 |
| JP | 5651036 B2 | 1/2015 |
| JP | 6784822 B2 | 11/2020 |
| JP | 2022527239 A | 6/2022 |
| KR | 10-2016-0064842 A | 6/2016 |
| KR | 10-2016-0094219 A | 8/2016 |
| KR | 10-2017-0041511 A | 4/2017 |
| KR | 10-1828068 B1 | 2/2018 |
| KR | 10-2020-0045124 A | 5/2020 |
| KR | 10-2137092 B1 | 7/2020 |
| KR | 10-2250772 B1 | 5/2021 |
| KR | 10-2264330 B1 | 6/2021 |
| KR | 10-2021-0112630 A | 9/2021 |
| KR | 10-2404321 B1 | 6/2022 |
| KR | 10-2022-0133010 A | 10/2022 |
| KR | 10-2022-0152700 A | 11/2022 |
| WO | 2018/105447 A1 | 6/2018 |

OTHER PUBLICATIONS

European Search Report dated Dec. 19, 2024, issued in European Application No. 22895796.5.

* cited by examiner

ELECTRONIC DEVICE FOR DETECTING MOISTURE

CROSS-REFERENCE TO RELATED APPLICATION(S)

This application is a continuation application, claiming priority under § 365(c), of an International application No. PCT/KR2022/011583, filed on Aug. 4, 2022, which is based on and claims the benefit of a Korean patent application number 10-2021-0161385, filed on Nov. 22, 2021, in the Korean Intellectual Property Office, and of a Korean patent application number 10-2021-0176613, filed on Dec. 10, 2021, in the Korean Intellectual Property Office, the disclosure of each of which is incorporated by reference herein in its entirety.

TECHNICAL FIELD

Various embodiments relate to an electronic device for detecting moisture.

BACKGROUND ART

As users' interest in health increases, an electronic device may obtain information on the user's body. The user may easily find a way to improve one's own physical condition by continuously monitoring one's physical condition through information provided from the electronic device.

As the user continuously wears the electronic device, the electronic device may be exposed to various situations that may cause a malfunction of the electronic device. For example, the electronic device may malfunction because a sensor fails to obtain accurate information from the user due to moisture or foreign substances penetrating into the inside.

The above information is presented as background information only to assist with an understanding of the disclosure. No determination has been made, and no assertion is made, as to whether any of the above might be applicable as prior art with regard to the disclosure.

DISCLOSURE

Technical Problem

An electronic device may include various types of sensors to obtain information on the user's body. For example, the electronic device may include a sensor including an electrode to obtain information on the user's physical condition. For example, when the electrode and other components of the electronic device are unintentionally electrically connected to each other due to moisture penetrating into the electronic device, the sensor may not obtain accurate information from a user and thus may malfunction. In order to prevent a malfunction of the sensor, the electronic device may include a sensor for detecting moisture, but the electronic device may not quickly respond to the malfunction of the sensor as it takes time to process data received from the sensor, and thus data detected from the sensor may not be trusted. The electronic device may detect moisture penetrating into the electronic device without including the sensor.

Various embodiments relate to the electronic device for detecting moisture.

The technical problems to be achieved in this document are not limited to those described above, and other technical problems not mentioned herein will be clearly understood by those having ordinary knowledge in the art to which the present disclosure belongs, from the following description.

Technical Solution

According to an embodiment, an electronic device may comprise a housing including a first surface, a second surface facing the first surface and facing a part of a user's body when the electronic device is worn to the user, and a conductive frame disposed between the first surface and the second surface and including a through-hole, a first electrode spaced apart from an inner surface of the through-hole, and movable within the through-hole, a part of the first electrode protruding to outside of the conductive frame, a second electrode disposed on the second surface, and contact with the part of the user's body when the electronic device is worn to the user, and a processor; wherein the processor may be configured to identify whether the first electrode is electrically disconnected to the conductive frame in response to identifying a designated event; obtain an information about the user' body through the first electrode and the second electrode, based on identifying the first electrode is electrically disconnected to the conductive frame; and refrain from obtaining the information based on identifying the first electrode is electrically connected to the conductive frame.

According to an embodiment, an electronic device may an electronic device may comprise a housing including a first surface, a second surface facing the first surface and facing a part of a user's body when the electronic device is worn to the user, and a conductive frame disposed between the first surface and the second surface and including a first through-hole and a second through-hole, a display disposed on the first surface, a first electrode spaced apart from an inner surface of the first through-hole, and movable within the first through-hole, and a part of the first electrode protruding to outside of the conductive frame, a second electrode disposed on the second surface, and contact with the part of the user's body when the electronic device is worn to the user, a third electrode spaced apart from an inner surface of the second through-hole, and movable within the second through-hole, and a part of the third electrode protruding to outside of the conductive frame, a fourth electrode disposed on the second surface spaced apart from the second electrode, and contact with the part of the user's body when the electronic device is worn to the user, and processor, wherein, the processor may be configured to identify whether the first electrode or the third electrode is electrically disconnected to the conductive frame, in response to identifying a designated event, obtain an information about the user' body through the first electrode, the second electrode, the third electrode, and the fourth electrode, based on identifying the first electrode is electrically disconnected to the conductive frame and identifying the third electrode is electrically disconnected to the conductive frame, and refrain from obtaining the information, based on identifying the first electrode is electrically connected to the conductive frame or the third electrode is electrically connected to the conductive frame.

Advantageous Effects

According to an embodiment, the electronic device can easily detect whether moisture has penetrated into the electronic device without including a separate additional sensor, by determining whether a conductive frame and a first electrode are electrically disconnected. According to an embodiment, the electronic device can smoothly obtain information on the user's body through electrodes by easily detecting whether moisture has penetrated.

The effects that can be obtained from the present disclosure are not limited to those described above, and any other effects not mentioned herein will be clearly understood by those having ordinary knowledge in the art to which the present disclosure belongs, from the following description.

DESCRIPTION OF THE DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

MODE FOR INVENTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
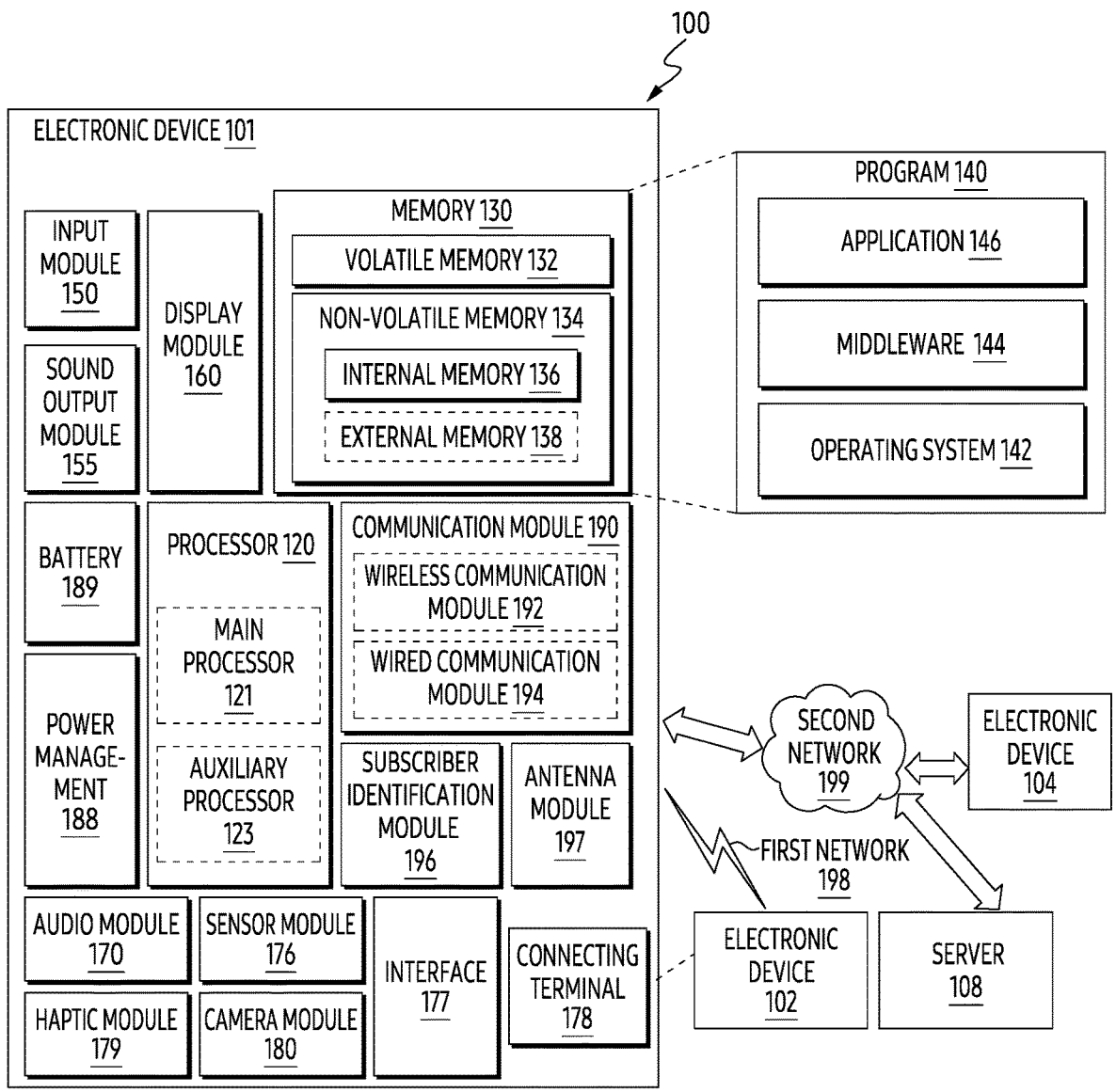
FIG. 1 is a block diagram of an electronic device in a network environment according to various embodiments.

FIG. 1 is a block diagram illustrating an electronic device 101 in a network environment 100 according to various embodiments.

Referring to FIG. 1, the electronic device 101 in the network environment 100 may communicate with an electronic device 102 via a first network 198 (e.g., a short-range wireless communication network), or at least one of an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™ wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2A:
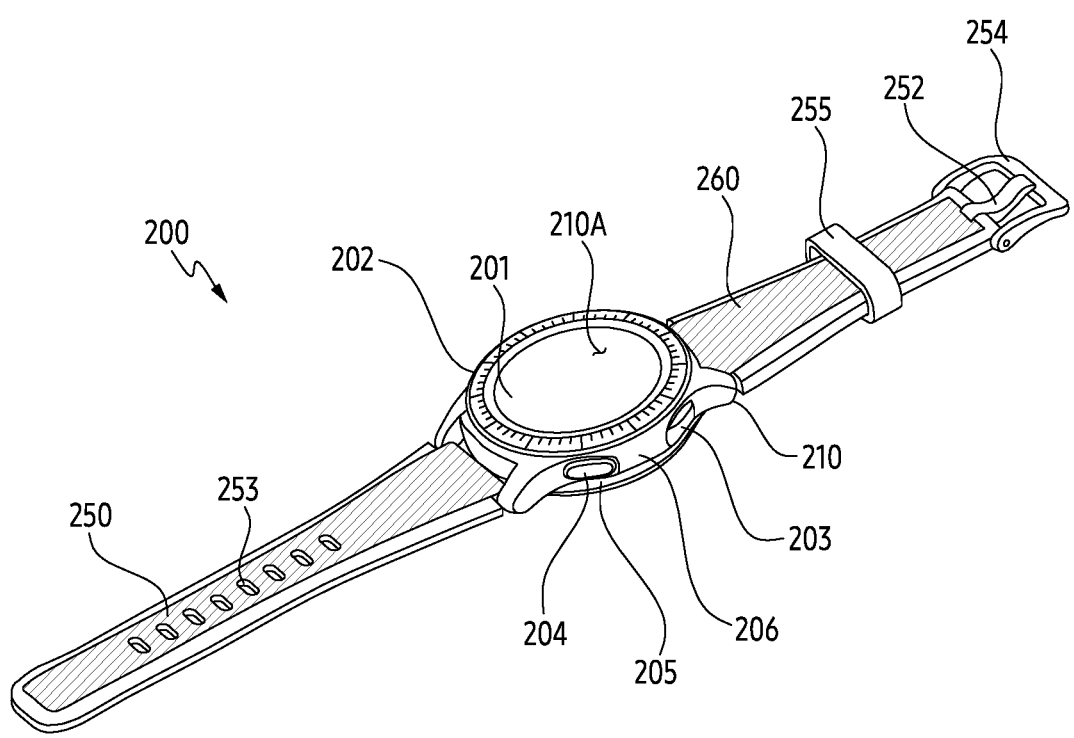
FIGS. 2A and 2B are perspective views of an electronic device according to an embodiment.
Figure 2B:
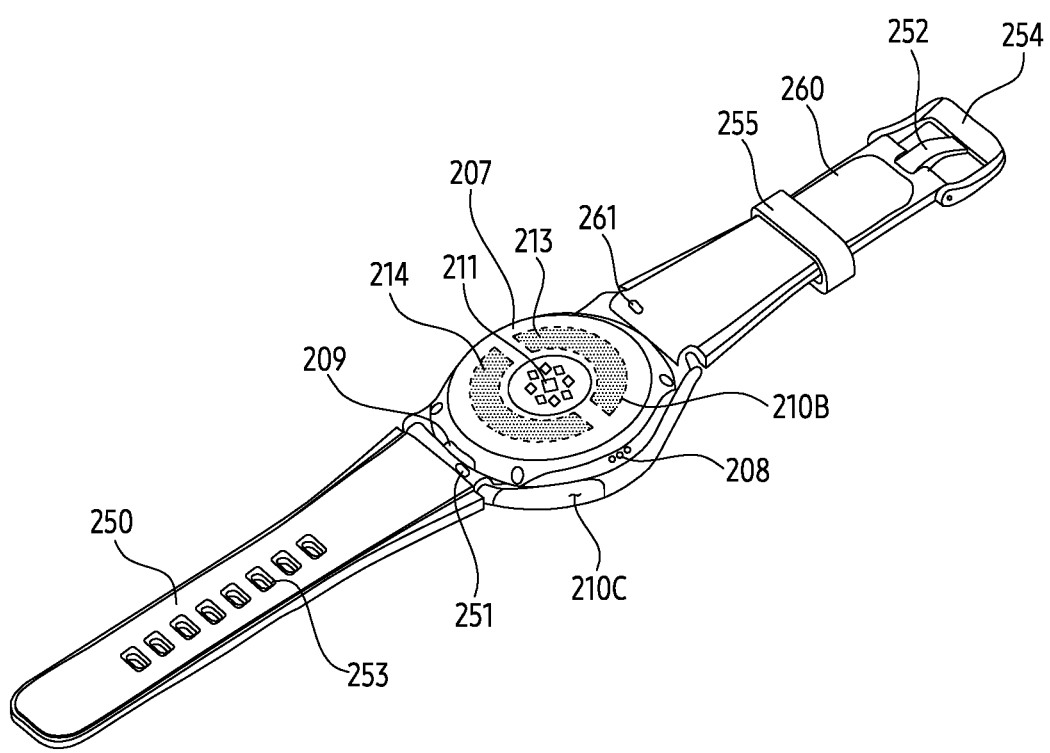

FIGS. 2A and 2B are perspective views of an electronic device according to an embodiment.

Referring to FIGS. 2A and 2B, an electronic device 200 (e.g., the electronic device 101 of FIG. 1) according to an embodiment may include a housing 210 including a first surface (or front surface) 210A, a second surface (or rear surface) 210B, and a side surface 210C surrounding the space between the first surface 210A and the second surface 210B and binding members 250 and 260 connected to at least a part of the housing 210 and configured to detachably attach the electronic device 200 to a part of the user's body (e.g., wrist, ankle, etc.). In another embodiment (not illustrated), the housing may also refer to a structure that forms at least a part of the first surface 210A, the second surface 210B, and the side surface 210C of FIG. 2A. According to an embodiment, at least a part of the first surface 210A may be implemented by a substantially transparent front plate 201 (e.g., glass plate or polymer plate including various coating layers). The second surface 210B may be implemented by a substantially opaque rear plate 207. The rear plate 207 may be made of, for example, coated or colored glass, ceramic, polymer, metal (e.g., aluminum, stainless steel (STS), or magnesium), or a combination of at least two of the materials. The side surface 210C may be coupled to the front plate 201 and the rear plate 207, and may be implemented by a side bezel structure (or "side member") 206 including metal and/or polymer. In some embodiments, the rear plate 207 and the side bezel structure 206 may be integrally formed and may include the same material (e.g., metal material such as aluminum). The binding members 250 and 260 may be made of various materials and may be made in various shapes. The binding members 250 and 260 may be made of woven fabric, leather, rubber, urethane, metal, ceramic, or a combination of at least two of the materials.

According to an embodiment, the electronic device 200 may include at least one of a display 220 (see FIG. 3), an audio module 205 and 208, a sensor module 211, a key input device 202, 203 and 204, and a connector hole 209. In some embodiments, the electronic device 200 may omit at least one of the components (e.g., the key input devices 202, 203 and 204, the connector hole 209, or the sensor module 211) or may further include another component.

The display 220 may be exposed, for example, through a substantial portion of the front plate 201. The shape of the display 220 may correspond to the shape of the front plate 20, such as circular (shown in FIG. 2A), oval, or polygonal. The display 220 may be coupled to or adjacent to a touch sensing circuit, a pressure sensor capable of measuring the strength (pressure) of touches, and/or a fingerprint sensor.

The audio modules 205 and 208 may include a microphone hole 205 and a speaker hole 208, a microphone for obtaining external sound may be disposed inside the microphone hole 205, and in some embodiments, a plurality of microphones may be disposed to detect the direction of the sound. The speaker hole 208 may be used with an external speaker and a receiver for phone calls. In some embodiments, the speaker hole 208 and the microphone hole 205 may be implemented as a single hole, or a speaker (e.g., piezo speaker) may be included without the speaker hole 208.

The sensor module 211 may generate electrical signal(s) or data value(s) corresponding to internal operating state(s) of the electronic device 200 or external environmental state(s). The sensor module 211 may include, for example, a biometric sensor module 211 (e.g., heart-rate monitor (HRM) sensor) disposed on the second surface 210B of the housing 210. The electronic device 200 may further include at least one sensor module not shown, such as a gesture sensor, a gyro sensor, a pressure sensor, a magnetic sensor, an acceleration sensor, a grip sensor, a color sensor, an infrared sensor, a biometric sensor, a humidity sensor, and/or an illumination sensor.

The sensor module 211 may include electrode regions 213 and 214 forming a part of the surface of the electronic device 200 and a bio-signal detection circuit (not shown) electrically connected to the electrode regions 213 and 214. For example, the electrode regions 213 and 214 may include the first electrode region 213 and the second electrode region 214 disposed on the second surface 210B of the housing 210. The sensor module 211 may be configured such that the electrode regions 213 and 214 obtain electrical signal(s) from a part of the user's body, and the bio-signal detection circuit may detect biometric information of the user based on the electrical signal(s).

The key input devices 202, 203, and 204 may include a wheel key 202 disposed on the first surface 210A of the housing 210 and rotatable in at least one direction, and/or side key buttons 203 and 204 disposed on the side surface 210C of the housing 210. The wheel key may have a shape corresponding to the shape of the front plate 201. In another embodiment, the electronic device 200 may not include some or all of the above-described key input devices 202, 203, and 204, and the not included key input devices 202, 203, and 204 may be implemented in other forms such as soft keys on the display 220. The connector hole 209 may accommodate a connector (e.g., USB connector) for transmitting and receiving power and/or data to and from external electronic devices and may include another connector hole (not illustrated) capable of accommodating a connector for transmitting and receiving audio signals to and from an external electronic device. The electronic device 200 may further include, for example, a connector cover (not illustrated) that covers at least a part of the connector hole 209 and blocks the inflow of external foreign material into the connector hole.

The binding members 250 and 260 may be attached to at least a part of the housing 210 and may be user-detachable from the housing 210 using locking members 251, 261. The binding members 250 and 260 may include one or more of a fixing member 252, a fixing member fastening hole 253, a band guide member 254, and a band fixing ring 255.

The fixing member 252 may be configured to fix the housing 210 and the binding members 250 and 260 to a part of the user's body (e.g., wrist, ankle, etc.). The fixing member fastening hole 253 may correspond to the fixing member 252 to fix the housing 210 and the binding members 250 and 260 to the part of the user's body. The band guide member 254 may be configured to limit movement range of the fixing member 252 when the fixing member 252 is fastened to the fixing member fastening hole 253, so that the binding members 250 and 260 are attached to be in close contact with the part of the user's body. The band fixing ring 255 may limit the range of movement of the binding members 250 and 260 when the fixing member 252 and the fixing member fastening hole 253 are fastened.

Figure 3:
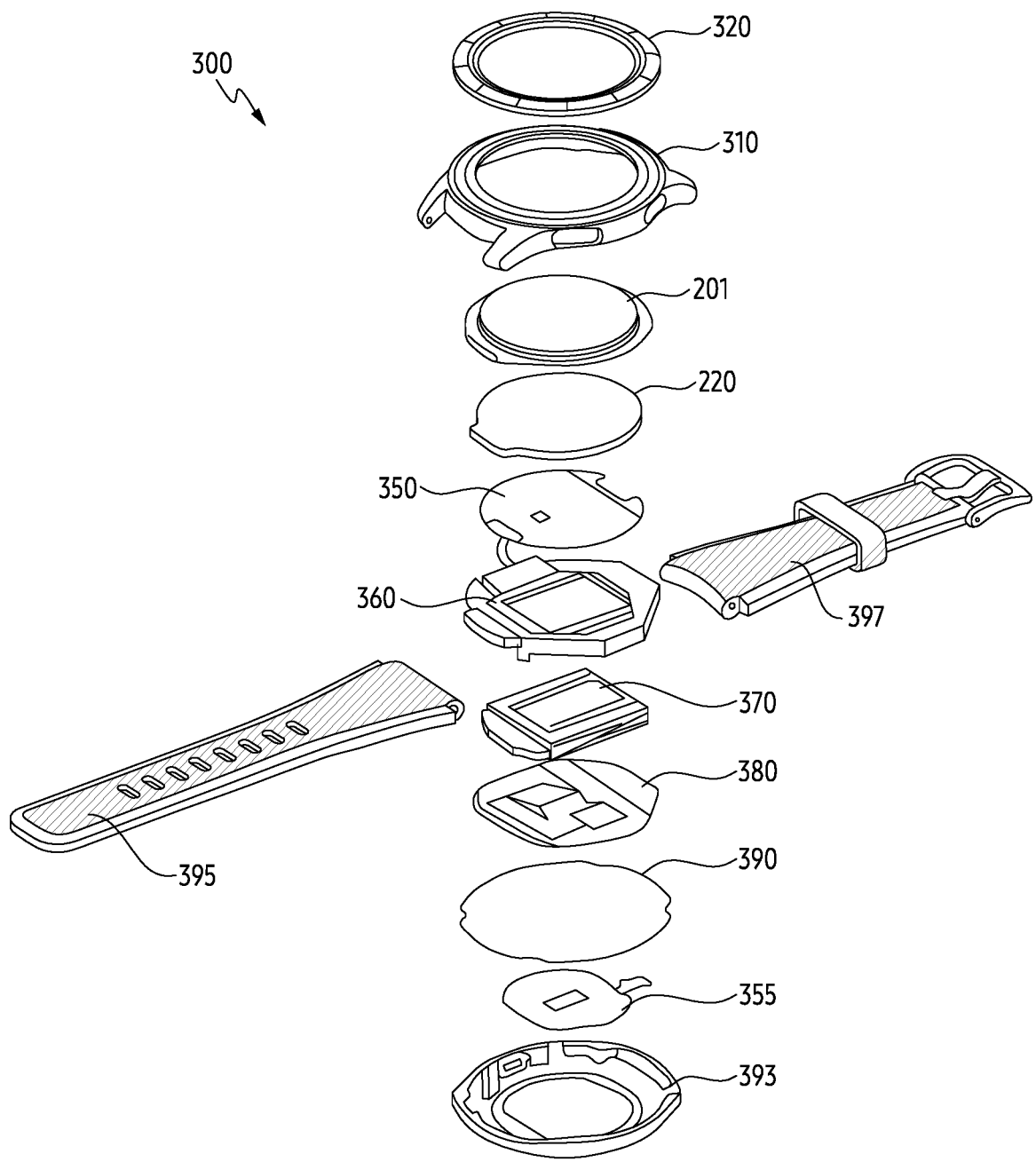
FIG. 3 is an exploded perspective view of an electronic device according to an embodiment.

FIG. 3 is an exploded perspective view of an electronic device according to an embodiment.

Referring to FIG. 3, an electronic device 300 (e.g., the electronic device 101 of FIG. 1, the electronic device 200 of FIG. 2A and/or FIG. 2B) may include a side bezel structure 310, a wheel key 320, a front plate 201, a display 220, a first antenna 350, a second antenna 355, a support member 360 (e.g., a bracket), a battery 370, a printed circuit board 380, a sealing member 390, and binding members 395 and 397. At least one of the components of the electronic device 300 may be the same as or similar to at least one of the components of the electronic device 200 of FIGS. 1, 2A, and/or 2B, and repeated description thereof will be omitted. The support member 360 may be disposed inside the electronic device 300 to be connected to the side bezel structure 310 or may be integrated with the side bezel structure 310. The support member 360 may be made of, for example, metal material and/or non-metal (e.g., polymer) material. The display 220 may be coupled to one surface of the support member 360, and the printed circuit board 380 may be coupled to the other surface of the support member 360. A processor, a memory, and/or an interface may be mounted on the printed circuit board 380. The processor may include, for example, one or more of a central processing unit, an application processor, a graphic processing unit (GPU), an application processor sensor processor, or a communication processor.

The memory may include, for example, a volatile memory or a nonvolatile memory. The interface may include, for example, a high definition multimedia interface (HDMI), a universal serial bus (USB) interface, an SD card interface, and/or an audio interface. The interface may electrically or physically connect the electronic device 300 to an external electronic device, for example, and may include a USB connector, an SD card/MMC connector, or an audio connector.

The battery 370 is a device for supplying power to at least one component of the electronic device 300, and may include, for example, a non-rechargeable primary battery, a rechargeable secondary battery, or a fuel battery. At least a part of the battery 370 may be disposed on substantially the same plane as, for example, the printed circuit board 380. The battery 370 may be integrally disposed inside the electronic device 200 or may be detachably coupled to the electronic device 200.

The first antenna 350 may be disposed between the display 220 and the support member 360. The first antenna 350 may include, for example, a near field communication (NFC) antenna, a wireless charging antenna, and/or a magnetic secure transmission (MST) antenna. The first antenna 350 may, for example, perform short-range communication with an external device, wirelessly transmit and receive power required for charging, and transmit short-range communication signal or an electromagnetic signal including payment data. In another embodiment, an antenna structure may be formed by at least a portion of the side bezel structure 310 and/or a part of the support member 360 or a combination thereof.

The second antenna 355 may be disposed between the printed circuit board 380 and the rear plate 393. The second antenna 355 may include, for example, a near field communication (NFC) antenna, a wireless charging antenna, and/or a magnetic secure transmission (MST) antenna. For example, the second antenna 355 may perform short-range communication with an external device, wirelessly transmit and receive power required for charging, and may transmit a short-range communication signal or an electromagnetic signal including payment data. In another embodiment, an antenna structure may be formed by at least a portion of the side bezel structure 310 and/or a part of the rear plate 393 or a combination thereof.

The sealing member 390 may be positioned between the side bezel structure 310 and the rear plate 393. The sealing member 390 may be configured to block moisture and foreign material flowing into the space surrounded by the side bezel structure 310 and the rear plate 393 from the outside.

Figure 4A:
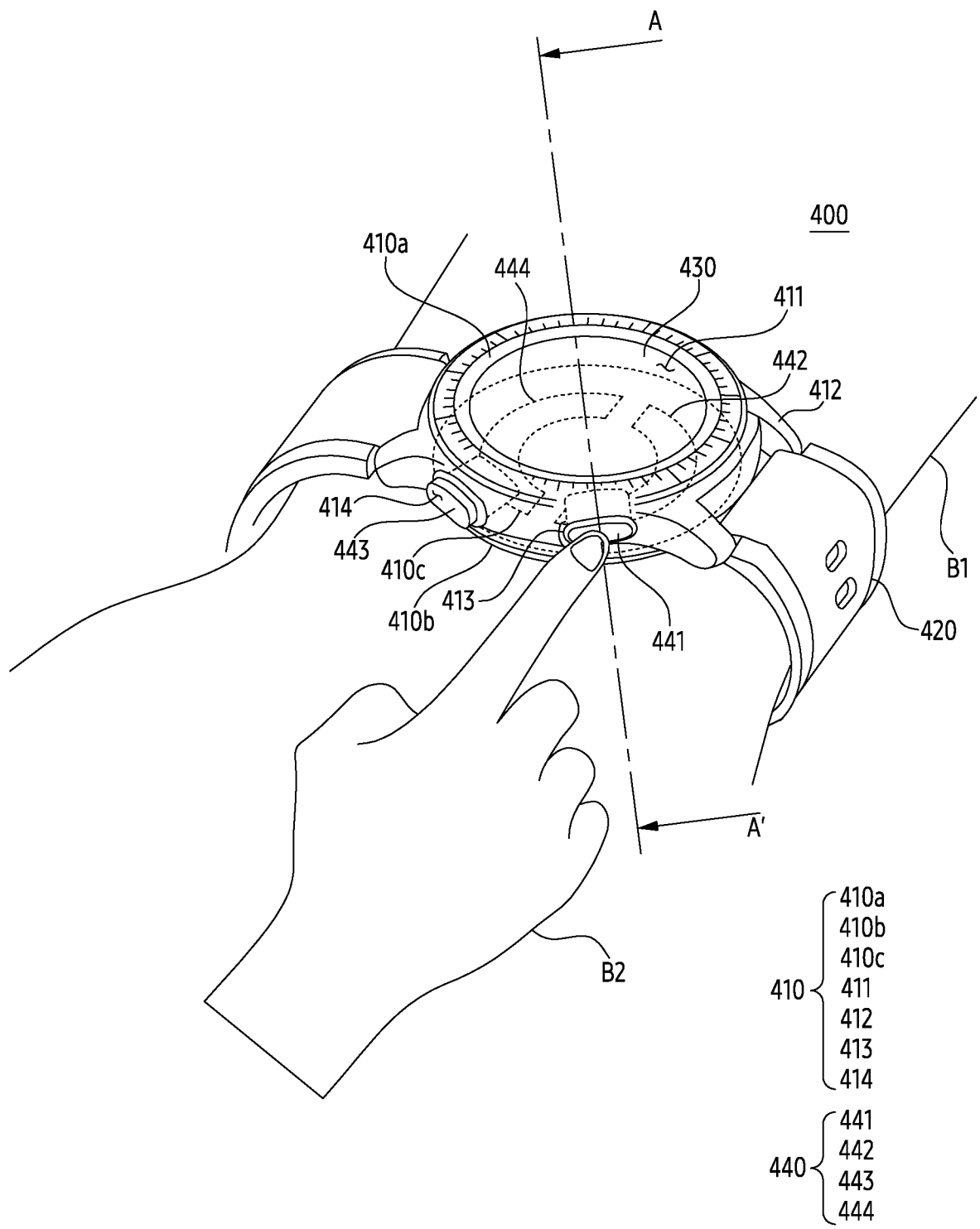
FIG. 4A is a perspective view of a second surface of an electronic device according to an embodiment.
Figure 4B:
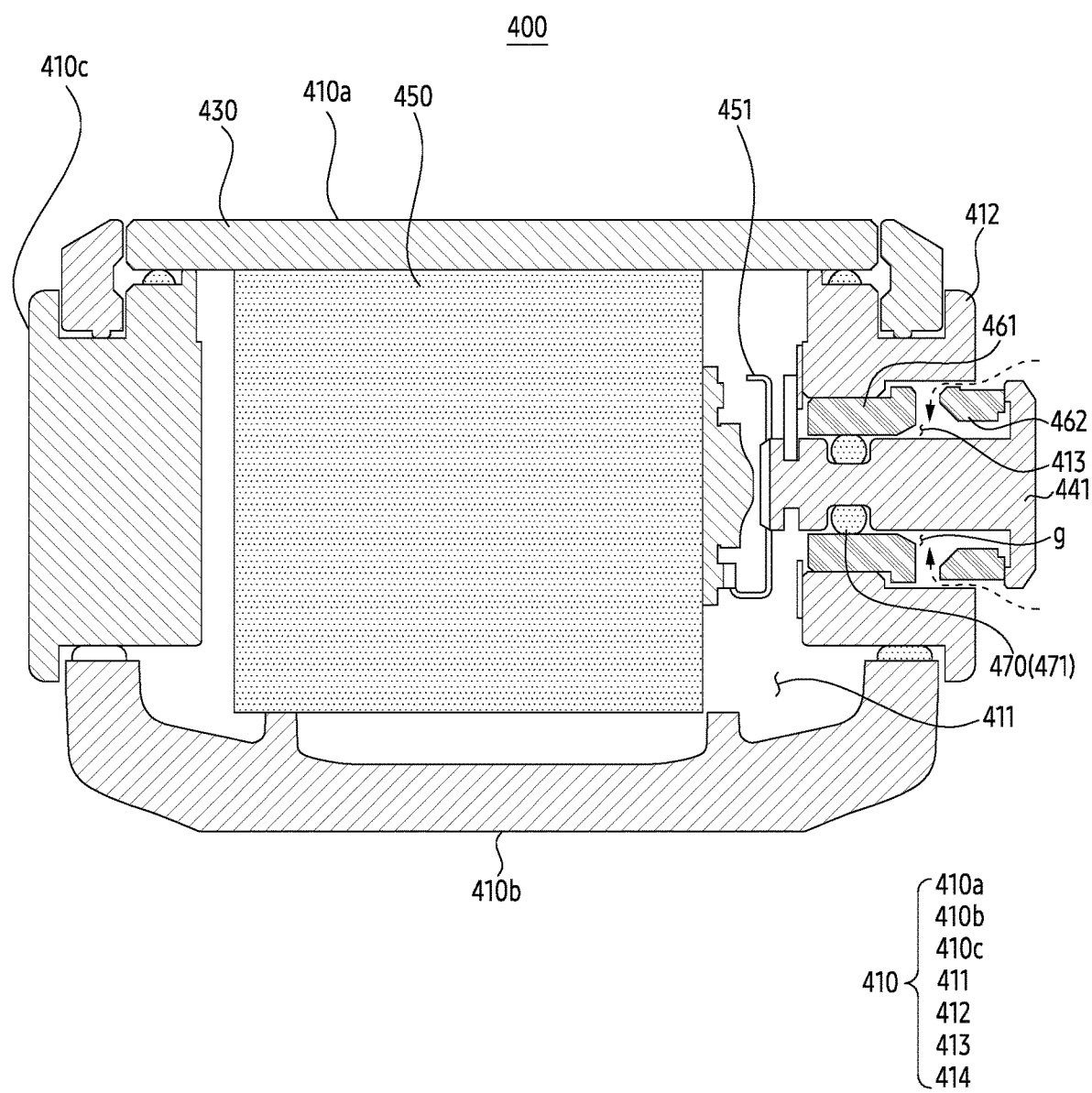
FIG. 4B is a cross-section view illustrating an example in which an electronic device is cut along A-A' of FIG. 4A according to an embodiment.

FIG. 4A is a perspective view of a second surface of an electronic device according to an embodiment, and FIG. 4B is a cross-section view illustrating an example in which an electronic device is cut along A-A' of FIG. 4A according to an embodiment.

Referring to FIGS. 4A and 4B, an electronic device 400 (e.g., electronic device 101 of FIG. 1, electronic device 200 of FIG. 2A and/or 2B, or electronic device 300 of FIG. 3) may include a housing 410 (e.g., housing 210 in FIG. 2A), a binding member 420 (e.g., binding members 250 and 260 of FIG. 2A and/or 2B), a display 430 (e.g., display 220 of FIG. 3), a plurality of electrodes 440, an electronic component 450, a non-conductive member 460, and a sealing member 470. According to an embodiment, when worn by a user, the electronic device 400 may contact a part of the user's body (e.g., a wrist or an ankle).

The housing 410 may form the overall appearance of the electronic device 400. According to an embodiment, the housing 410 may include a first surface 410a and a second surface 410b facing the first surface 410a. The first surface 410a and the second surface 410b may be substantially the same as the first surface 210A of FIG. 2A and the second surface 210B of FIG. 2B, respectively. According to an embodiment, when the electronic device 400 is worn by a user, the second surface 410b may face a part of the user's body.

According to an embodiment, the housing 410 may include an inner space 411 and a conductive frame 412. The inner space 411 may accommodate various components of the electronic device 400. For example, the inner space 411 may accommodate an electronic component 450 capable of performing various functions of the electronic device 400. The inner space 411 may be an empty space formed inside the housing 410. For example, the inner space 411 may refer to a space surrounded by the first surface 410a, the second surface 410b, and a side surface 410c extending from an edge of the first surface 410a and the second surface 410b and connecting the first surface 410a and the second surface 410b. The conductive frame 412 may form at least a part of the side surface 410c of the housing 410. According to an embodiment, the conductive frame 412 may be disposed between the first surface 410a and the second surface 410b of the housing 410, and may connect the first surface 410a and the second surface 410b. The conductive frame 412 may form the inner space 411 together with the first surface 410a and the second surface 410b, and may protect various components of the electronic device 400 accommodated in the inner space 411. For example, the conductive frame 412 may form at least a part of a side member (e.g., side member 206 of FIG. 2A). According to an embodiment, at least a part of the conductive frame 412 may be made of a metal material (e.g., aluminum, stainless steel (STS), or magnesium). For example, the conductive frame 412 may be entirely made of a metal material, or may be made of a combination of a metal and a non-conductive material (e.g., glass, ceramic, or polymer).

According to an embodiment, the conductive frame 412 may include a first through hole 413 and a second through hole 414 connecting the inner space 411 of the housing 410 to the outside of the electronic device 400. According to an embodiment, the first through hole 413 and the second through hole 414 may be extended to form, from the inner space 411 of the housing 410, to the outside of the conductive frame 412, in a direction substantially perpendicular to a direction toward the first surface 410a.

When the electronic device 400 is worn by a user, the binding member 420 may support the electronic device 400 so as not to deviate from the wearing position by contacting a part B1 of the user's body. The binding member 420 may be substantially the same as the binding members 260 and 270 of FIGS. 2A and/or 2B. The binding member 420 may be defined as a strap for fixing the electronic device 400 to the user's body. According to an embodiment, the binding member 420 may be rotatably coupled to the housing 410. For example, the binding member 420 may be hinged to a part of the conductive frame 412 to be rotatable with respect to the conductive frame 412. According to an embodiment, at least a part of the binding member 420 may be made of a metal material. For example, the binding member 420 may be entirely made of a metal (e.g., aluminum, stainless steel (STS), or magnesium), or a material including a combination of the metal and a non-conductive material (e.g., silicon, fiber, glass, ceramic, or polymer). As another example, the binding member 420 may be entirely made of a non-conductive material.

The display 430 may output visual information. The user may check information on the state of the electronic device 400 or information on the state of the user through the visual information output by the display 430. According to an embodiment, the display 430 may include a touch sensor configured to detect a user's touch or a pressure sensor that detects a magnitude of a force generated by the user's touch. When the display 430 includes the touch sensor or the pressure sensor, the display 430 may receive a user's touch input. For example, the touch sensor may be printed on a layer in the panel of the display 430 to be integrally formed with the display panel. For another example, the touch sensor may be formed of a film including a touch electrode and attached to one of the layers forming the display panel.

The plurality of electrodes 440 may receive an electrical signal for obtaining information on the user's body. For example, the plurality of electrodes 440 may receive an electrical signal for obtaining at least one of information on the user's electrocardiogram (ECG), information on the user's bioelectrical impedance, information on the user's electromyogram (EMG), and information on the skin electrodermal activity (EDA). The information on skin electrodermal activity (EDA) may include, for example, at least one of a galvanic skin response (GSR), an electrothermal response (EDR), a psychogalvanic reflex (PGR), a skin conduction response (SCR), and a symmetric skin response (SSRS). According to an embodiment, the plurality of electrodes 440 may include a first electrode 441, a second electrode 442, a third electrode 443, and/or a fourth electrode 444 spaced apart from each other. Each of the first electrode 441 and the third electrode 443 may be inserted into the first through hole 413 and the second through hole 414 of the conductive frame 412, and the second electrode 442 and the fourth electrode 444 may be disposed on the second surface 410b of the housing 410. For example, the first electrode 441 and the third electrode 443 may extend to the outside of the electronic device 400 in a direction substantially perpendicular to a direction in which the first surface 410a faces from the inner space 411 of the housing 410, respectively. For another example, the second electrode 442 and the fourth electrode 444 may be disposed to face each other on the second surface 410b of the housing 410.

According to an embodiment, the first electrode 441 and the third electrode 443 may function as a key button by forming at least a part of the key buttons 203 and 204 of FIG. 2A. When the first electrode 441 or the third electrode 443 is pressed by a user, the electronic device 400 may perform a designated function in response to the pressure of the first electrode 441 or the third electrode 443. For example, the electronic device 400 may perform an on/off function of power of the electronic device 400 or a wake-up/sleep function in response to pressure of the first electrode 441 or the third electrode 443. According to an embodiment, the first electrode 441 and the third electrode 443 may be related with different functions of the electronic device 400. According to an embodiment, one of the first electrode 441, the second electrode 442, the third electrode 443, and the fourth electrode 444 may be omitted according to a function provided through the electronic device 400. For example, the electronic device 400 may omit one of the first electrode 441 and the third electrode 443 or omit one of the second electrode 442 and the fourth electrode 444, according to design necessity. When the third electrode 443 is unnecessary in the electronic device 400, the third electrode 443 may be configured to operate as a key button but not as an electrode.

According to an embodiment, a part of the first electrode 441 and the third electrode 443 may protrude to the outside of the conductive frame 412 and may move in the first through hole 413 and the second through hole 414, respectively. As the first electrode 441 and the third electrode 443 move in the first through hole 413 and the second through hole 414, respectively, the first electrode 441 and the third electrode 443 may provide a click feeling to the user of the electronic device 400. According to an embodiment, the first electrode 441 and the third electrode 443 may be spaced apart from the inner surfaces of the first through hole 413 and the second through hole 414 to be movable in the first through hole 413 and the second through hole 414, respectively. For example, each of the first electrode 441 and the third electrode 443 may be spaced apart from the first through hole 413 and the second through hole 414 in a direction substantially perpendicular to the extending direction of the first electrode 441 and the third electrode 443. For example, the shape of the side surface of the first electrode 441 may correspond to the inner surface of the first through hole 413. The side surface of the first electrode 441 and the inner surface of the first through hole 413 may be spaced apart from each other.

According to an embodiment, the plurality of electrodes 440 may be electrically separated in a state before contacting parts B1 and B2 of the user's body. When the plurality of electrodes 440 contact parts B1 and B2 of the user's body, an electrical closed circuit may be formed by the plurality of electrodes 440 and the parts B1 and B2 of the user's body. As the electrical closed circuit is formed, the plurality of electrodes 440 may receive an electrical signal generated in the user's body or emit a current to a part B1 and B2 of the user through a part thereof and receive a current returning from the part B1 and B2 of the user through the other part.

According to an embodiment, the plurality of electrodes 440 may receive an electrical signal generated in the user's body to obtain information on the user's electrocardiogram by contacting different parts B1 and B2 of the user's body. For example, when the electronic device 400 is worn on the user's left hand, the second electrode 442 disposed on the second surface 410b may contact the left hand that is a part B1 of the user's body, and the first electrode 441 may contact the right hand that is the other part B2 of the user's body. When the first electrode 441 and the second electrode 442 contact different parts B1 and B2 of the user's body, an electrical closed circuit pass through the user's heart may be formed by the first electrode 441, the second electrode 442, and the different parts B1 and B2 of the body. The first electrode 441 and the second electrode 442 may obtain information on the user's electrocardiogram by receiving an active potential generated in the myocardium by the user's heartbeat via the electrical closed circuit pass through the user's heart.

According to an embodiment, the plurality of electrodes 440 may emit a current via parts B1 and B2 of the user's body and receive a current returning again in order to obtain information on the user's bio-electric resistance by contacting different each parts B1 and B2 of the user's body. For example, when the electronic device 400 is worn on the user's left hand, as the second electrode 442 and the fourth electrode 444 disposed on the second surface 410b contact with different regions of the left hand, which is a part B1 of the user's body and the first electrode 441 and the third electrode 443 contact different fingers of the right hand, which is the other part B2 of the user's body, the electrical closed circuit may be formed in the first electrode 441, the second electrode 442, the third electrode 443, the fourth electrode 444, and different parts B1 and B2 of the body. When the electrical closed circuit is formed, as an alternating current is applied from a part of the first electrode 441, the second electrode 442, the third electrode 443, and the fourth electrode 444 to different parts B1 and B2 of the user's body and the current is received to another part of the first electrode 441, the second electrode 442, the third electrode 443, and the fourth electrode 444, the electronic device 400 may obtain information on the user's bioelectrical resistance.

Referring to FIG. 4B, the electronic component 450 may include components disposed in the housing 410 and performing an operation of the electronic device 400. According to an embodiment, the electronic component 450 may include at least one sensor (e.g., the sensor module 220 of FIG. 2B), wherein at least one sensor may be configured to be electrically connected to a processor (e.g., the processor 120 in FIG. 1) that perform the overall operation of the electronic device 400, and the plurality of electrodes 440, and detect information on the user's body through an electrical signal received from the plurality of electrodes 440. According to an embodiment, the processor may be operatively coupled to the conductive frame 412, the display 430, and a plurality of electrodes 440. According to an embodiment, the at least one sensor may be, for example, at least one of an electrocardiogram (ECG) sensor, a bioelectrical impedance analysis (BIA) sensor, an electromyogram (EMG) sensor, and an electrodermal activity (EDA) sensor.

According to an embodiment, the electronic component 450 may include a contact part 451 forming an electrical contact with the first electrode 441. The contact part 451 may not form an electrical contact with the first electrode 441 in a state where the first electrode 441 is not pressed by a user. When the first electrode 441 is pressed by a user, the contact part 451 may form an electrical contact with the first electrode 441 by contacting the first electrode 441. As the contact part 451 and the first electrode 441 form an electrical contact, the electrical signal may be transmitted from the contact unit 451 to the processor, and the processor may perform a designated function of the electronic device 400 based on receiving the electrical signal. For example, the contact unit 451 may refer to a spring contact connector, but is not limited thereto and may be changed into various components capable of forming an electrical contact with the first electrode 441.

The non-conductive member 460 may electrically separate the conductive frame 412 from the first electrode 441. The non-conductive member 460 may be made of an electrically non-conductive material such as plastic. According to an embodiment, the non-conductive member 460 may include a first non-conductive member 461 and a second non-conductive member 462 that coupled to the conductive frame 412 in order to contact the inner surface of the first through hole 413, and the first electrode 441 and spaced apart from each other. For example, the first non-conductive member 461 may surround one area of the first electrode 441 close to the inner space 411 and may be fixed to the inner surface of the first through hole 413. For another example, the second non-conductive member 462 may be coupled to one end of the first electrode 441 facing the outside of the electronic device 400 and may move together with the first electrode 441. According to an embodiment, an air gap g may be formed between the first non-conductive member 461 and the second non-conductive member 462 so that the first non-conductive member 461 and the second non-conductive member 462 are spaced apart from each other in a state before the first electrode 441 is pressed by the user. The second non-conductive member 462 may move together with the first electrode 441, according to a user's pressure, to contact the first non-conductive member 461. The first non-conductive member 461 and the second non-conductive member 462 may function as a stopper for limiting a moving distance of the first electrode 441 by contacting according to movement of the first electrode 441.

The sealing member 470 may prevent foreign substances from penetrating into the inner space 411 from the outside of the electronic device 400 by sealing the first through hole 413. For example, the first sealing member 471 may surround one area of the first electrode 441 positioned within the first through hole 413 inside the first non-conductive member 461. The first sealing member 471 may contact the first non-conductive member 461 and the first electrode 441 by surrounding one region of the first electrode 441, thereby sealing the first through hole 413. For example, the sealing member 470 may refer an o-ring, but is not limited thereto.

According to an embodiment, in order to obtain information on the user's body, the processor may be configured to identify whether the user's body is in contact with the plurality of electrodes 440. For example, the processor may identify whether a user's body contacts the first electrode 441 and the second electrode 442 based on identifying impedance values between the first electrode 441 and the second electrode 442. Since the user's body may serve as a conductor, when the part B2 of the user's body contacts the first electrode 441, an impedance value between the first electrode 441 and the second electrode 442 may be lower than when the part B2 of the user's body is not in contact with the first electrode 441. The processor may identify the impedance value between the first electrode 441 and the second electrode 442, and when the identified impedance value is equal to or less than a reference value, it may determine that a user's body contacts the first electrode 441 and the second electrode 442. According to an embodiment, while obtaining information on the user's body, the processor may be configured to continuously monitor an impedance value between the plurality of electrodes 440 in order to identify whether the user's body is in contact with the plurality of electrodes 440.

According to an embodiment, the processor may identify whether the first electrode 441 is electrically disconnected from the conductive frame 412 in response to identifying the designated event. The designated event may mean receiving an input signal of a user requesting information on the user's body or detecting that the designated mode of the electronic device 400 is changed to another designated mode. According to an embodiment, the processor may identify whether the first electrode 441 and the conductive frame 412 are electrically disconnected based on identifying whether an impedance value between the first electrode 441 and the conductive frame 412 is equal to or less than a reference value. For example, moisture may penetrate into the first through hole 413 along a fine gap between the conductive frame 412 and the second conductive member 462 and may be positioned in the air gap g between the first non-conductive member 461 and the second non-conductive member 462. The moisture moved into the air gap g may contact the first electrode 441 and the conductive frame 412 to electrically connect the first electrode 441 and the conductive frame 412. When the first electrode 441 and the conductive frame 412 are electrically connected to each other, an impedance value between the first electrode 441 and the conductive frame 412 may be measured to be lower than that when the first electrode 441 and the conductive frame 412 are electrically disconnected. According to an embodiment, the processor of the electronic device 400 may identify whether the first electrode 441 and the conductive frame 412 are electrically disconnected by identifying that the impedance value between the first electrode 441 and the conductive frame 412 is equal to or less than a reference value.

According to an embodiment, the processor may be configured to obtain information on the user's body through the first electrode 441 and the second electrode 442 based on identifying that the first electrode 441 is electrically disconnected from the conductive frame 412, and refrain from obtaining information on the user's body based on identifying that the first electrode 441 is electrically connected to the conductive frame 412. For example, when the first electrode 441 and the conductive frame 412 are connected by moisture, the first electrode 441 may form an indirect electrical connection to a part B1 of the body via the conductive frame 412 and/or the binding member 420 in contact with part B1 of the body. When the first electrode 441 forms an indirect electrical connection with the part B1 of the body, an impedance value between the first electrode 441 and the second electrode 442 may be less than or equal to a reference value in a state where the second electrode 442 contacts the part B1 of the user's body. When an impedance value equal to or lower than the reference value is identified, the processor may initiate an operation of obtaining information on the user's body and may malfunction, since normal contact with different parts of the body (B1, B2) and abnormal contact with part of the body (B1) are not distinguished by impedance values. For example, in the case of obtaining information on the user's electrocardiogram, since only a part B1 of the user's body comes into contact with the first electrode 441 and the second electrode 442 when the conductive frame 412 and the first electrode 441 are electrically connected, the electrical closed circuit formed by the first electrode 441 and the second electrode 442 does not pass through the user's heart, and the processor may not accurately obtain information on the user's electrocardiogram. Since the processor does not obtain information on the electrocardiogram, the processor may repeatedly perform an operation of determining whether the body is in contact again to cause a malfunction.

According to the above-described embodiment, the electronic device 400 may identify whether the processor electrically disconnects the first electrode 441 and the conductive frame 412, and the electronic device 400 may prevent a malfunction of the processor by stopping obtaining information on the user's body when the electrical connection between the first electrode 441 and the conductive frame 412 is identified.

Meanwhile, although the structure of FIG. 4B has been described with respect to the first through hole 413 and the first electrode 441, the description of FIG. 4B may be equally applied to the second through hole 414 and the third electrode 443. For example, the non-conductive member 460 may include a third non-conductive member (not illustrated) and a fourth non-conductive member (not illustrated) that coupled to the conductive frame 412 to contact the inner surface of the second through hole 414, and the third electrode 443 and spaced apart from each other. For another example, the sealing member 470 may further include a second sealing member (not illustrated) that seals the second through hole 414 by surrounding the third electrode 443.

Figure 5A:
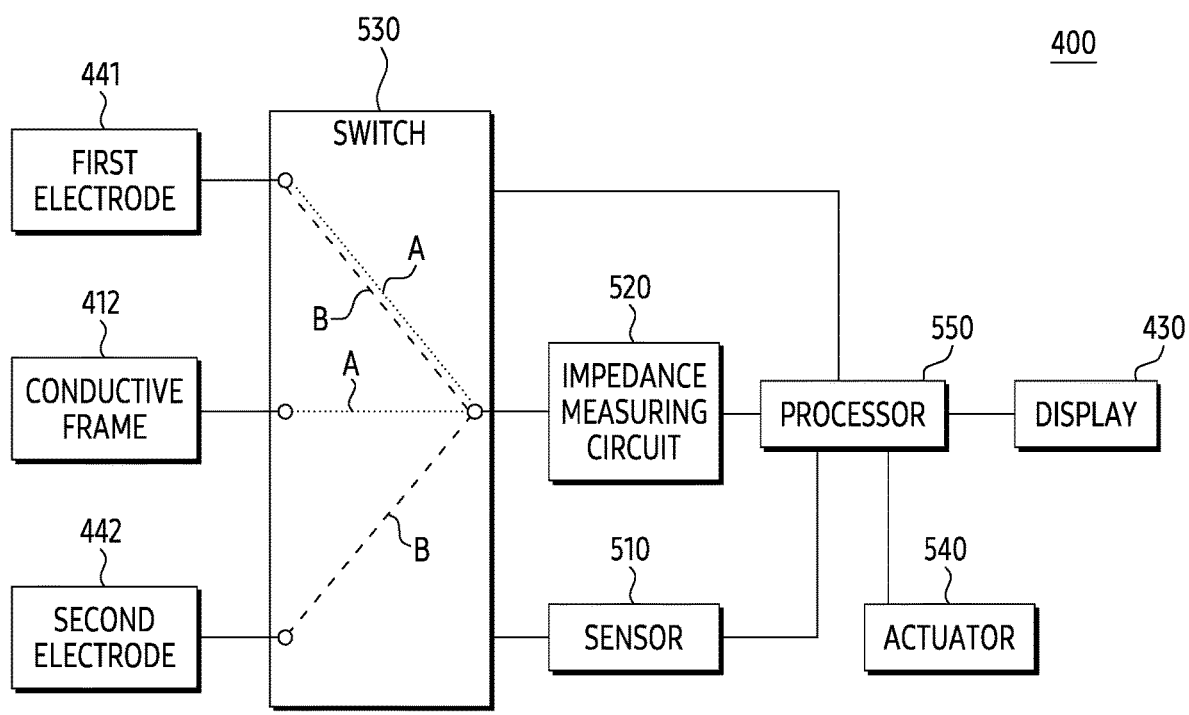
FIG. 5A is a block diagram of an electronic device according to an embodiment.
Figure 5B:
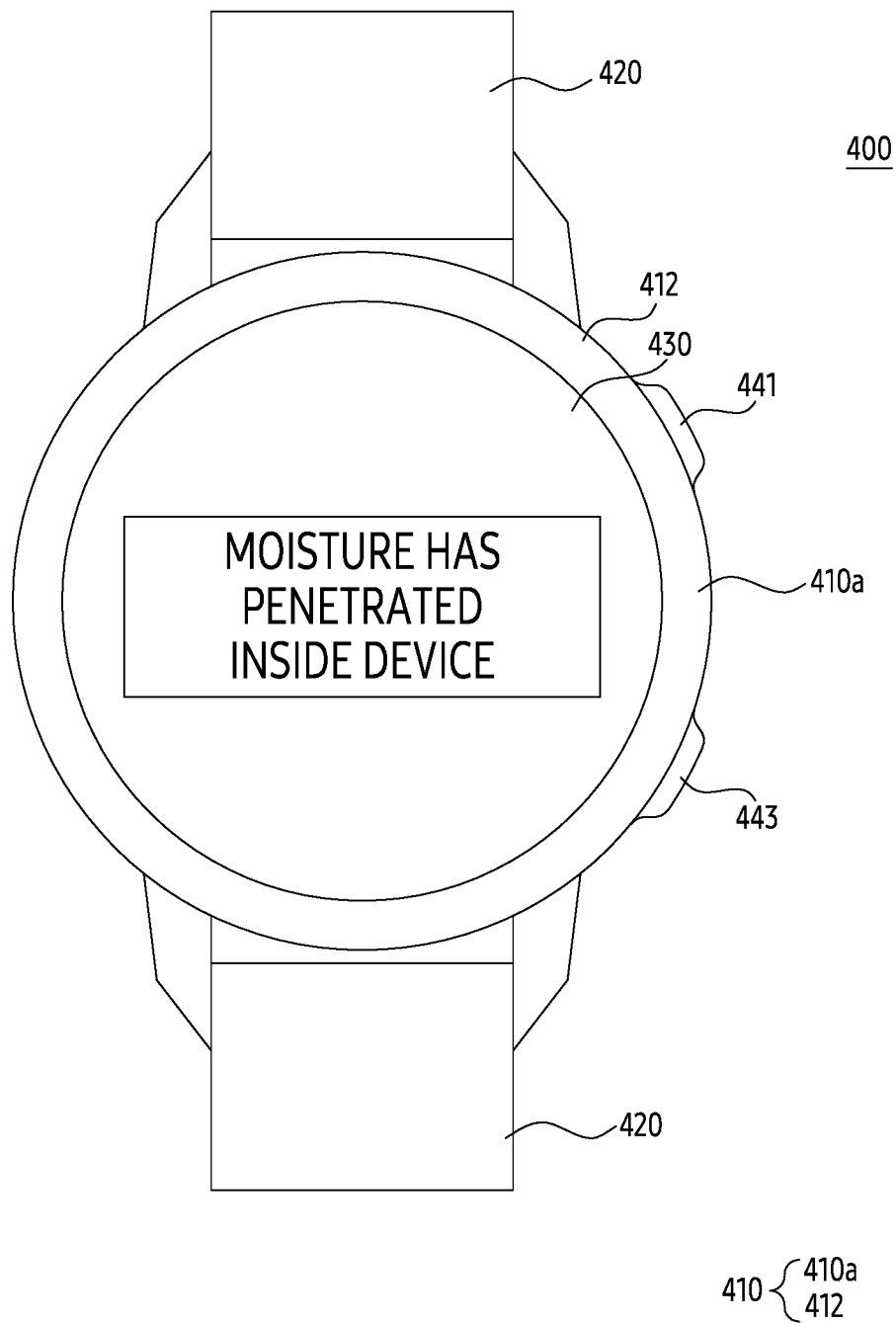
FIG. 5B is a diagram illustrating an example of providing a notification of whether an electronic device is submerged, according to an embodiment.

FIG. 5A is a block diagram of an electronic device according to an embodiment, and FIG. 5B is a diagram illustrating an example of providing a notification of whether an electronic device is submerged, according to an embodiment.

According to an embodiment, referring to FIGS. 5A and 5B, the electronic device 400 may include a conductive frame 412, a display 430, a first electrode 441, a second electrode 442, a sensor 510, an impedance measurement circuit 520, at least one switch 530, an actuator 540, and a processor 550. The conductive frame 412 of FIGS. 5A and 5B, the display 430, the first electrode 441, and the second electrode 442 may be substantially the same as the conductive frame 412 of FIGS. 4A and/or 4B, the display 430, the first electrode 441, and the second electrode 442, respectively, and thus repeated descriptions thereof will be omitted.

The sensor 510 may be configured to obtain information on a user's body by receiving an electrical signal received from the first electrode 441 and the second electrode 442. The sensor 510 may obtain information on the user's body and transmit the obtained information to the processor 550. For example, the sensor 510 may be at least one of an electrocardiogram (ECG) sensor, a bioelectrical impedance analysis (BIA) sensor, an electroencephalogram (EEG) sensor, and a galvanic skin response (GSR) sensor.

The impedance measurement circuit 520 may obtain impedance values between the conductive frame 412, the first electrode 441, and the second electrode 442. For example, the impedance measurement circuit 520 may be electrically connected to the conductive frame 412 and the first electrode 441, thereby measuring an impedance value between the conductive frame 412 and the first electrode 441. For another example, the impedance measurement circuit 520 may be electrically connected to the first electrode 441 and the second electrode 442, thereby measuring an impedance value between the first electrode 441 and the second electrode 442.

The at least one switch 530 may selectively connect at least one of the conductive frame 412, the first electrode 441, and the second electrode 442 to the impedance measurement circuit 520. According to an embodiment, the at least one switch 530 may switch to a first state A connecting the conductive frame 412 and the first electrode 441 to the impedance measurement circuit 520 and a second state B connecting the first electrode 441 and the second electrode 442.

The actuator 540 may discharge moisture penetrating into the first through hole (e.g., the first through hole 413 of FIGS. 4A and/or 4B) or the second through hole (e.g., the second through hole 414 of FIG. 4A) to the outside of the electronic device 400. According to an embodiment, the actuator 540 may be disposed in the housing (e.g., the housing 410 of FIG. 4A and/or FIG. 4B) to vibrate the electronic device 400 or a designated component (e.g., the sound output module 155 of FIG. 1) in the electronic device 400, thereby discharging moisture to the outside of the electronic device 400.

The processor 550 may be operatively coupled to the display 430, the sensor 510, the impedance measurement circuit 520, at least one switch 530, and the actuator 540. The processor 550 may identify whether the first electrode 441 is electrically disconnected from the conductive frame 412 in response to identifying the designated event. According to an embodiment, the designated event may include receiving an input signal of a user requesting information on a user's body. For example, when the user wants to obtain information on the body, the user may execute software (e.g., an application) used to provide information on the body by touching the display 430 or pressing the first electrode 441. When execution (e.g., application execution) of software used to provide information on the body is detected, the processor 550 may perform an operation for identifying whether the first electrode 441 is electrically disconnected from the conductive frame 412. According to another embodiment, the designated event may include identifying that the mode of the electronic device 400 is changed from the first designated mode to the second designated mode. The first designated mode may mean a swimming mode of the electronic device 400, and the second designated mode may mean another operation mode of the electronic device 400 other than the swimming mode. The swimming mode of the electronic device 400 may mean an operating state of the electronic device 400 when a user swims while wearing the electronic device 400. For example, when the electronic device 400 enters the swimming mode, the processor 550 may control the display 430 so that a touch input through the display 430 is not received. According to another embodiment, the designated event may include identifying whether moisture has penetrated into the electronic device 400 through a moisture detecting sensor (e.g., an atmospheric pressure sensor).

According to an embodiment, the processor 550 may electrically connect the impedance measurement circuit 520 to the first electrode 441, and the conductive frame 512 through the at least one switch 530 by switching the at least one switch 530 to the first state A, in response to identifying the designated event. The processor 550 may identify whether the first electrode 441 is electrically disconnected from the conductive frame 412 based on the impedance value between the first electrode 441 and the conductive frame 512 obtained through the impedance measurement circuit 520. For example, the processor 550 may identify that the first electrode 441 is electrically connected to the conductive frame 412 based on identifying that the impedance value between the first electrode 441 and the conductive frame 412 is equal to or less than a reference value. For another example, the processor 550 may identify that the first electrode 441 is electrically disconnected from the conductive frame 412 based on identifying that the impedance value between the first electrode 441 and the conductive frame 412 is greater than the reference value.

According to an embodiment, the processor 550 may be configured to obtain information on a user's body through the first electrode 441 and the second electrode 442, based on identifying that the first electrode 441 is electrically disconnected from the conductive frame 412. For example, the processor 550 may electrically connect the first electrode 441 and the second electrode 442 to the impedance measurement circuit 520 through the at least one switch 530 by switching the at least one switch 530 from the first state A to the second state B based on identifying that the first electrode 441 is electrically disconnected from the conductive frame 412. As the at least one switch 530 is switched from the first state A to the second state B, the impedance measurement circuit 520 and the conductive frame 412 may be electrically disconnected. According to an embodiment, the sensor 510 may obtain information on a user's bio-signal (e.g., an electrocardiogram) based on the electrical signals received by the first electrode 441 contacting a part of the body (e.g., part B1 of the body in FIG. 4A) and the second electrode 442 contacting another part of the body (e.g., part B2 of the body in FIG. 4A). The processor 550 may receive information on the user's bio-signal (e.g., ECG) acquired by the sensor 510 and notify the user of information on the user's bio-signal (e.g., ECG) through the display 430.

According to an embodiment, the processor 550 may identify whether the user's body contacts the first electrode 441 and the second electrode 442 based on identifying whether the impedance value between the first electrode 441 and the second electrode 442 is equal to or less than a reference value through the impedance measurement circuit 520. For example, when it is identified that the impedance value between the first electrode 441 and the second electrode 442 is less than or equal to the reference value, the processor 550 may obtain information on the user's body through the sensor 510. The processor 550 may notify the user of information on the user's body by outputting information on the user's body obtained through the sensor 510 to the display 430. For another example, the processor 550 may provide a notification to the user to check the physical contact state based on identifying that the impedance value between the first electrode 441 and the second electrode 442 exceeds the reference value. The processor 550 may provide a visual notification for guiding contact with the body through the display 430, a tactile notification that induces physical contact by vibrating the electronic device 400 through the actuator 540, or an audible notification that induces physical contact through the sound output module (e.g., the sound output module 155 of FIG. 1).

According to an embodiment, the processor 550 may be configured to refrain from obtaining information on the user's body based on identifying that the first electrode 441 is electrically connected to the conductive frame 412. When identifying that the first electrode 441 is electrically connected to the conductive frame 412, the processor 550 may provide a notification that the electronic device 400 is submerged. For example, the processor 550 may provide a visual notification to the user that moisture has penetrated into the electronic device 400 through the display 430. For another example, the processor 550 may provide a visual guide so that the user may remove moisture in the electronic device 400 through the display 430. The visual guide provided through the display 430 may indicate an operation in which a user may remove moisture by shaking the electronic device 400 or may refer to a picture or a video indicating a method of drying the electronic device 400. For another example, the processor 550 may remove moisture in the electronic device 400 by operating the actuator 540 to vibrate the electronic device 400.

As described above, according to an embodiment, the electronic device 400 may identify whether the electronic device 400 is submerged by identifying whether the first electrode 441 is electrically disconnected from the conductive frame 412 without including an additional sensor. For example, the electronic device 400 may include an impedance measurement circuit 520 to identify whether the user's body maintains contact with the first electrode 441 and the second electrode 442. The electronic device 400 according to an embodiment may easily detect whether the electronic device 400 is submerged by connecting the conductive frame 412 and the first electrode 441 to the impedance measurement circuit 520 for checking the body contact state, and thus may not include a separate sensor for detecting submerging. As it is unnecessary to include a separate additional sensor, the electronic device 400 according to an embodiment may include a relatively simple circuit structure.

Figure 6:
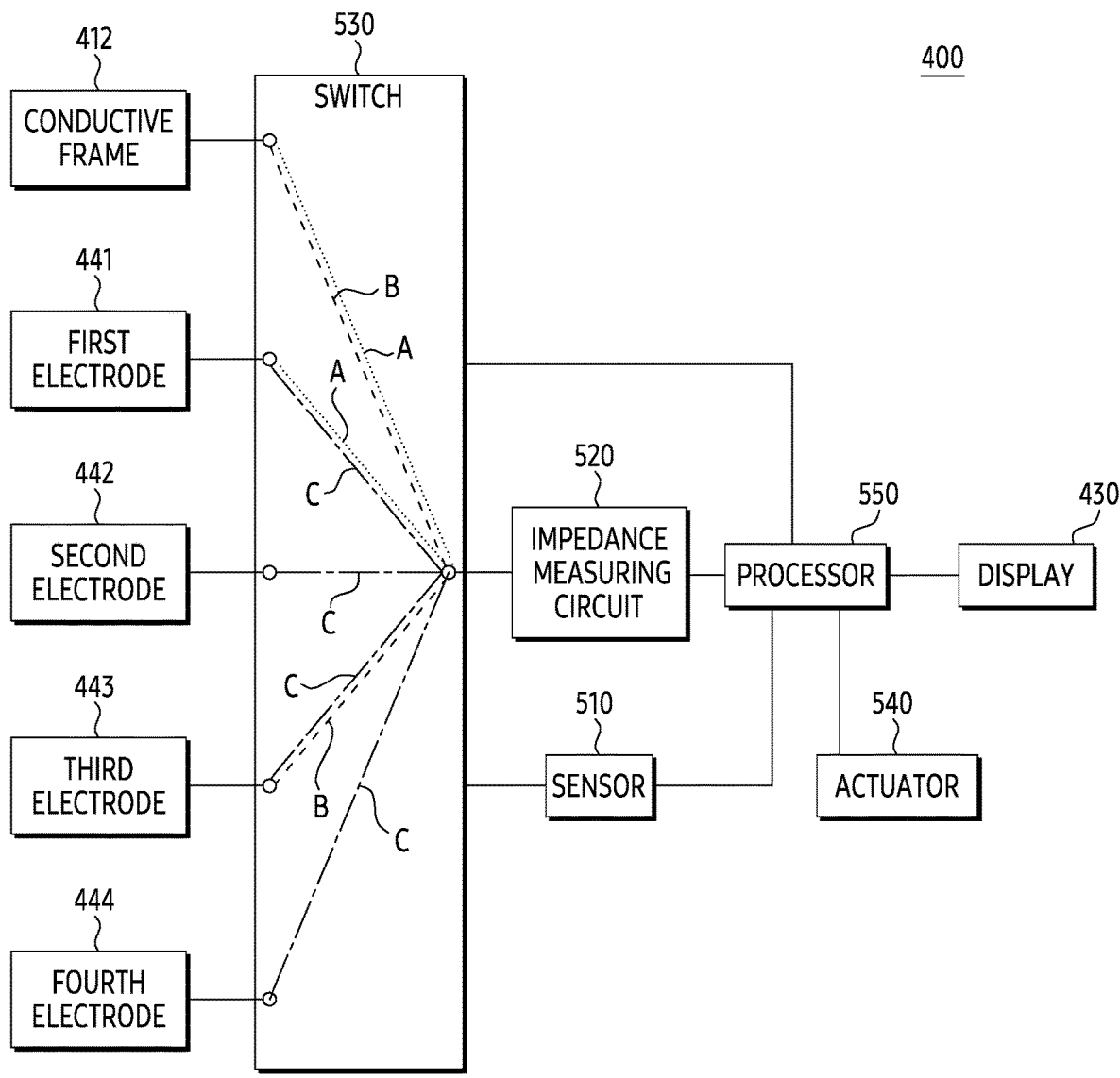
FIG. 6 is a block diagram of an electronic device according to an embodiment.

FIG. 6 is a block diagram of an electronic device according to an embodiment.

Referring to FIG. 6, the electronic device 400 according to an embodiment may include a conductive frame 412, a display 430, a first electrode 441, a second electrode 442, a third electrode 443, a fourth electrode 444, a sensor 510, an impedance measurement circuit 520, at least one switch 530, an actuator 540, and a processor 550.

The conductive frame 412 of FIG. 6, the display 430, the first electrode 441, the second electrode 442, the third electrode 443, and the fourth electrode 444 may be substantially the same as the conductive frame 412 of FIGS. 4A and/or 4B, display 430, the first electrode 441, the second electrode 442, the third electrode 443, and the fourth electrode 444, respectively, and the sensor 510 of FIG. 6, the impedance measurement circuit 520, at least one switch 530, the actuator 540, and the processor 550 may be substantially the same as the sensor 510 of FIGS. 5A, the impedance measurement circuit 520, at least one switch 530, the actuator 540, and the processor 550, respectively, and thus, repeated descriptions thereof will be omitted.

According to an embodiment, the sensor 510 may be configured to obtain information on a user's body by receiving electrical signals received from the first electrode 441, the second electrode 442, the third electrode 443, and the fourth electrode 444.

The impedance measurement circuit 520 may obtain impedance values between the conductive frame 412, the first electrode 441, the second electrode 442, the third electrode 443, and the fourth electrode 444. For example, the impedance measurement circuit 520 may be electrically connected to the conductive frame 412 and the first electrode 441, thereby measuring an impedance value between the conductive frame 412 and the first electrode 441. For another example, the impedance measurement circuit 520 may be electrically connected to the conductive frame 412 and the third electrode 442, thereby measuring an impedance value between the conductive frame 412 and the third electrode 442. For another example, the impedance measurement circuit 520 may be electrically connected to the first electrode 441, the second electrode 442, the third electrode 443, and the fourth electrode 444 through at least one switch 530, thereby measuring impedance values between the first electrode 441, the second electrode 442, the third electrode 443, and the fourth electrode 444.

According to an embodiment, the at least one switch 530 may selectively connect at least one of the conductive frame 412, the first electrode 441, the second electrode 442, the third electrode 443, and the fourth electrode 444 to the impedance measurement circuit 520. According to an embodiment, the at least one switch 530 may switch to a first state A connecting the conductive frame 412 and the first electrode 441 to the impedance measurement circuit 520, a second state B connecting the conductive frame 412 and the third electrode 443 to the impedance measurement circuit 520, and a third state C that connects the first electrode 441, the second electrode 442, the third electrode 443, and the fourth electrode 444 to the impedance measurement circuit 520.

According to an embodiment, the processor 550 may identify whether the first electrode 441 or the third electrode 443 is electrically disconnected from the conductive frame 412 in response to identifying a designated event. For example, in response to identifying the designated event, the processor 550 may electrically connect the impedance measurement circuit 520 to the first electrode 441, and the conductive frame 512 through at least one switch 530 by switching the at least one switch 530 to the first state A. The processor 550 may identify whether the first electrode 441 is electrically disconnected from the conductive frame 412 based on the impedance value between the first electrode 441 and the conductive frame 512 obtained through the impedance measurement circuit 520. For another example, in response to identifying the designated event, the processor 550 may electrically connect the impedance measurement circuit 520 to the third electrode 443, and the conductive frame 412 through the at least one switch 530 by switching the at least one switch 530 to the second state B. The processor 550 may identify whether the third electrode 443 is electrically disconnected from the conductive frame 412 based on the impedance value between the third electrode 443 and the conductive frame 512 obtained through the impedance measurement circuit 520. According to an embodiment, the order in which the first electrode 441 and the conductive frame 412 are connected to the impedance measurement circuit 520 and the third electrode 443 and the conductive frame 412 are connected may be arbitrarily changed.

According to an embodiment, the processor 550 may be configured to obtain information on a user's body through the first electrode 441, the second electrode 442, the third electrode 443, and the fourth electrode 444, based on identifying that the first electrode 441 is electrically disconnected from the conductive frame 412 and the third electrode 443 is electrically disconnected from the conductive frame 412. For example, by switching at least one switch 530 from the first state A or the second state B to the third state C, the processor 550 may electrically connect the first electrode 441, the second electrode 442, the third electrode 443, and the fourth electrode 444 to the impedance measurement circuit 520. As the at least one switch 530 is switched to the third state C, the impedance measurement circuit 520 and the conductive frame 412 may be electrically disconnected. According to an embodiment, the sensor 510 may obtain information on the user's bio-electric resistance based on the electrical signals received to the first electrode 441, the second electrode 442, the third electrode 443, and the fourth electrode 444. The processor 550 may receive information on the user's bio-electrical resistance from the sensor 510 and notify the user of information on the user's bio-electrical resistance through the display 430.

According to an embodiment, the processor 550 may be configured to refrain from obtaining information on a user's body based on identifying that the first electrode 441 is electrically connected to the conductive frame 412, or that the third electrode 443 is electrically connected to the conductive frame 412. For example, the processor 550 may identify that the first electrode 441 or the third electrode 443 is electrically connected to the conductive frame 412 Based on identifying that an impedance value between the first electrode 441 and the conductive frame 412 or an impedance value between the third electrode 443 and the conductive frame 412 is less than or equal to a reference value. When identifying that the first electrode 441 or the third electrode 443 is electrically connected to the conductive frame 412, the processor 550 may provide a notification to the user that the electronic device 400 is submerged. For example, the processor 550 may provide a visual notification to the user that moisture has penetrated into the electronic device 400 through the display 430. For example, the processor 550 may provide a visual notification to the user that moisture has penetrated into the electronic device 400 through the display 430. For another example, the processor 550 may remove moisture in the electronic device 400 by operating the actuator 540 to vibrate the electronic device 400.

As described above, according to an embodiment, the electronic device 400 may identify whether the electronic device 400 is submerged by identifying whether the first electrode 441 or the third electrode 443 is electrically disconnected from the conductive frame 412 without including an additional sensor. For example, the electronic device 400 may include an impedance measurement circuit 520 to identify whether a user's body maintains contact with the first electrode 441, the second electrode 442, the third electrode 443, and the fourth electrode 444. The electronic device 400 according to an embodiment may not include a separate sensor for detecting submerging, since it is possible to easily detect whether the electronic device 400 is submerged by connecting the conductive frame 412 to the first electrode 441 or third electrode 443 to the impedance measurement circuit 520 to check the physical contact condition. As a separate additional sensor is not required, the electronic device 400 according to an embodiment may include a relatively simple circuit structure.

Figure 7:
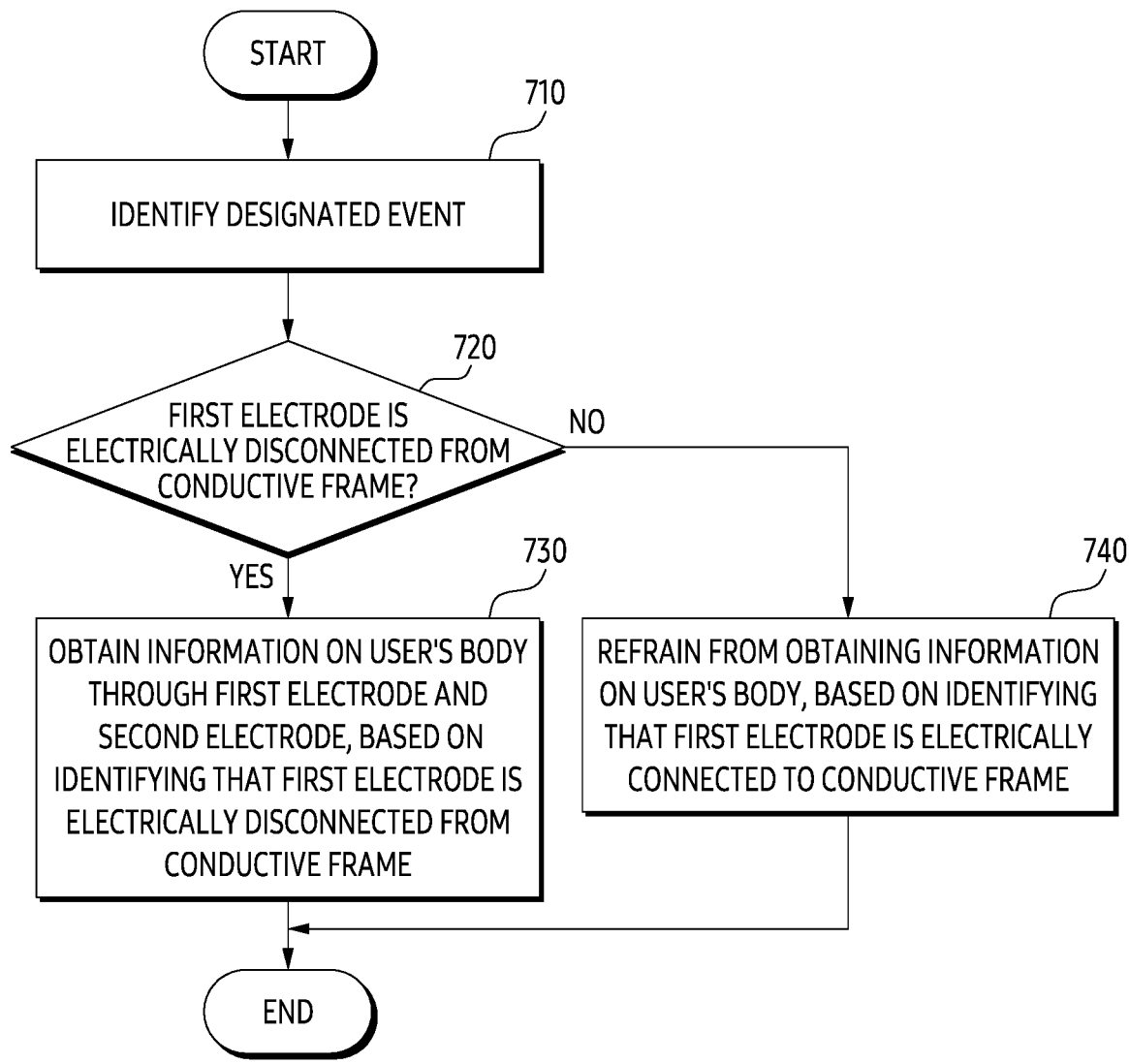
FIG. 7 illustrates an example of an operation of a processor of an electronic device, according to an embodiment.

FIG. 7 illustrates an example of an operation of a processor of an electronic device, according to an embodiment.

The operation illustrated in FIG. 7 may be performed by the electronic device 400 illustrated in FIGS. 4A, 4B, 5A, and/or 5B.

Referring to FIG. 7, in operation 710, an electronic device (e.g., a processor 550 of the electronic device 400 of FIG. 4A) may identify a designated event. According to an embodiment, the designated event may include receiving an input signal of a user requesting information on a user's body or changing a designated mode of the electronic device. For example, the designated event may include detecting execution of software (e.g., execution of an application) used to provide information on the body. As another example, the designated event may include identifying that the mode of the electronic device is changed from the first designated mode to the second designated mode. According to an embodiment, the first designated mode may mean a swimming mode of the electronic device, and the second designated mode may mean an operation mode of the electronic device other than the swimming mode.

In operation 720, the processor may identify whether the first electrode (e.g., the first electrode 441 of FIG. 4A) is electrically disconnected from the conductive frame (e.g., the conductive frame 412 of FIG. 4A) based on responding to the designated event. According to an embodiment, the processor may identify whether the first electrode is electrically disconnected from the conductive frame based on an impedance value between the first electrode and the conductive frame obtained through an impedance measurement circuit (e.g., the impedance measurement circuit 520 of FIG. 5A). For example, the processor may identify that the first electrode is electrically connected to the conductive frame when the impedance value between the first electrode and the conductive frame is less than or equal to the reference value. For another example, the processor may identify that the first electrode is electrically disconnected from the conductive frame when the impedance value between the first electrode and the conductive frame exceeds the reference value.

In operation 730, the processor may obtain information on a user's body through the first electrode and the second electrode (e.g., the second electrode 442 of FIG. 4A) based on identifying that the first electrode is electrically disconnected from the conductive frame. According to an embodiment, the processor may disconnect the conductive frame and the impedance measurement circuit through at least one switch (e.g., at least one switch 530 of FIG. 5A), and may electrically connect the impedance measurement circuit to the first electrode and the second electrode. According to an embodiment, the first electrode and the second electrode may receive an electrical signal generated in the user's body in order to obtain information on the user's bio signal by contacting different parts of the user's body (e.g., different parts of the body (B1, B2) in FIG. 4A). According to an embodiment, the first electrode and the second electrode may receive an electrical signal related to a user's bio-signal (e.g., ECG) by forming an electrical closed circuit pass through the user's heart with a part of the user's body.

In operation 740, the processor may refrain from obtaining information on the user's body based on identifying that the first electrode is electrically connected to the conductive frame. According to an embodiment, the processor may provide a user with a notification of whether the electronic device is submerged through a display (e.g., the display 430 of FIG. 4A). According to another embodiment, the processor may remove moisture penetrating into the electronic device by vibrating the electronic device through an actuator (e.g., the actuator 540 in FIG. 5A).

As described above, according to an embodiment, the electronic device 400 may identify whether the electronic device 400 is submerged by identifying whether the first electrode 441 or the third electrode 443 is electrically disconnected from the conductive frame 412 without including an additional sensor.

Figure 8:
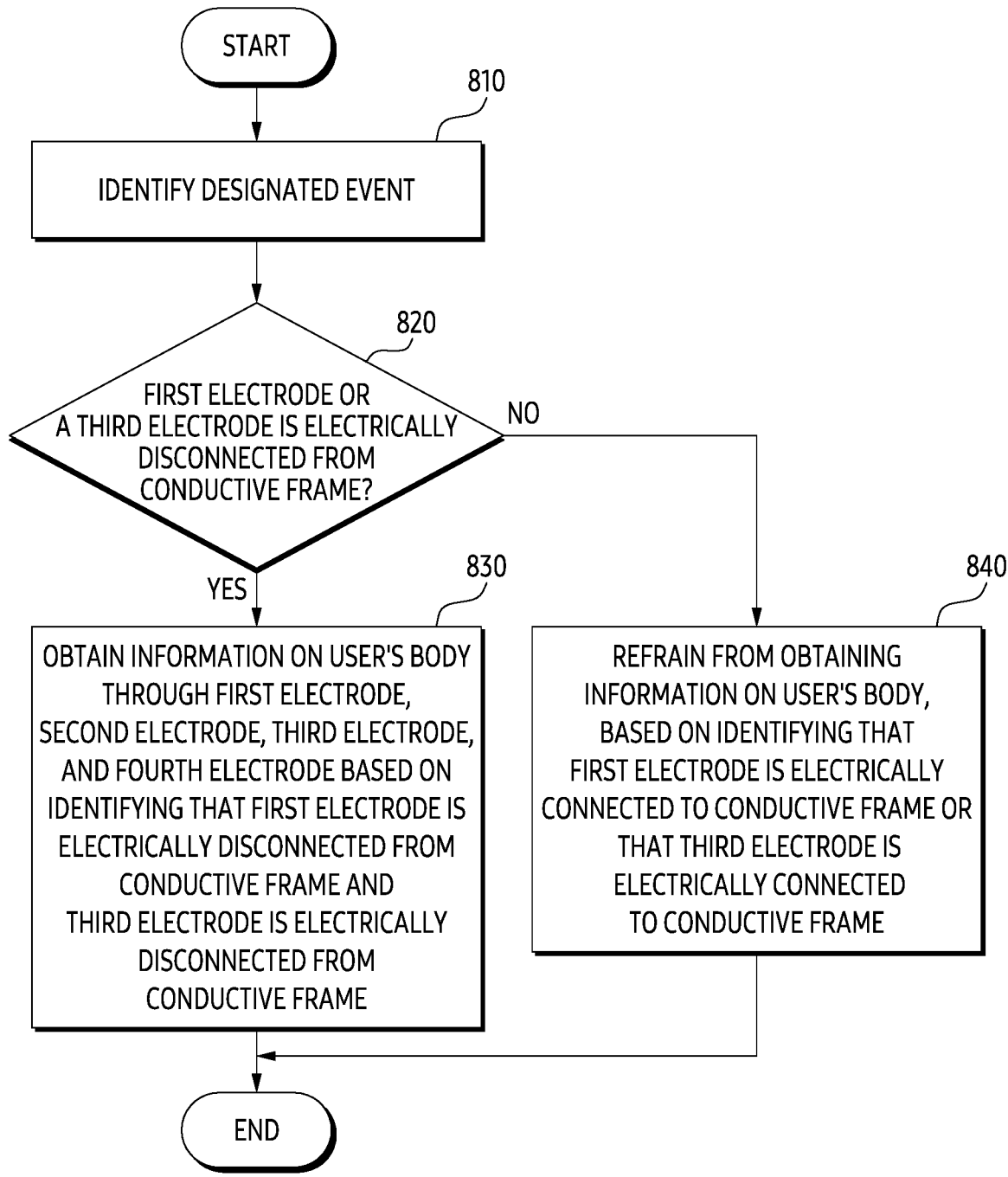
FIG. 8 illustrates an example of an operation of a processor of an electronic device, according to an embodiment.

FIG. 8 illustrates an example of an operation of a processor of an electronic device, according to an embodiment.

The operation illustrated in FIG. 8 may be performed by the electronic device 400 illustrated in FIGS. 4A, 4B, 5A, and/or 5B.

Referring to FIG. 8, operation 810 may be substantially the same as operation 710 of FIG. 7, and thus a repeated description thereof will be omitted.

In operation 820, in response to identifying a designated event, the processor (e.g., the processor 550 of FIG. 5A) may identify whether a first electrode (e.g., the first electrode 441 of FIG. 4A) or a third electrode (e.g., the third electrode 443 of FIG. 4A) is electrically disconnected from a conductive frame (e.g., the conductive frame 412 of FIG. 4A). According to an embodiment, the processor may identify whether the first electrode or the third electrode is electrically disconnected from the conductive frame, based on whether the impedance value between the first electrode and the conductive frame or between the third electrode and the conductive frame exceeds the reference value. For example, when an impedance value between the first electrode and the conductive frame or an impedance value between the third electrode and the conductive frame is less than or equal to a reference value, the processor may identify that the first electrode or the third electrode is electrically connected to the conductive frame.

In operation 830, the processor may obtain information on the user's body through the first electrode, the second electrode, the third electrode, and the fourth electrode based on identifying that the first electrode is electrically disconnected from the conductive frame and the third electrode is electrically disconnected from the conductive frame. According to an embodiment, the first electrode, the second electrode, the third electrode, and the fourth electrode may receive an electrical signal generated in the user's body in order to obtain information on the user's bio signal by contacting different parts of the user's body (e.g., different parts of the body B1 and B2 in FIG. 4A). For example, the second electrode and the fourth electrode may contact different areas of the left hand, which are part of the user's body (e.g., part B1 of the body illustrated in FIG. 4A), and the first electrode and the third electrode may contact different fingers of the right hand, which are another part of the user's body (e.g., the other part B2 of the body of FIG. 4A). The first electrode, the second electrode, the third electrode, and the fourth electrode contacting different parts of the user's body may form an electrical closed circuit together with different parts of the user's body. According to an embodiment, the processor may obtain information on the user's bio electrical resistance based on an electrical signal received by the first electrode, the second electrode, the third electrode, and the fourth electrode.

In operation 840, according to an embodiment, the processor may be configured to refrain from obtaining information on the user's body, based on identifying that the first electrode is electrically connected to the conductive frame or that the third electrode is electrically connected to the conductive frame. According to an embodiment, when identifying that the first electrode or the third electrode is electrically connected to the conductive frame, the processor may provide a user with a notification that the electronic device is submerged. For example, the processor may provide a visual notification to the user that moisture has penetrated into the electronic device (e.g., the electronic device 400 of FIG. 4A) through the display (e.g., the display 430 of FIG. 4A). For another example, the processor may remove moisture in the electronic device by operating the actuator (e.g., the actuator 540 of FIG. 5A) to vibrate the electronic device.

As described above, according to an embodiment, the electronic device may identify whether the electronic device is submerged by identifying whether the first electrode or the third electrode is electrically disconnected from the conductive frame without including an additional sensor.

According to an embodiment, an electronic device may comprise a housing (e.g. the housing 410 in FIG. 4A) including a first surface (e.g., the first face 410*a* of FIG. 4A), a second surface (e.g., the second face 410*b* of FIG. 4A), facing the first surface and facing a part of the user's body when the electronic device (e.g., the electronic device 400 of FIG. 4A) is worn to the user, and a conductive frame (e.g., the conductive frame 412 of FIG. 4A) disposed between the first surface and the second surface and including a through-hole (e.g., the first through hole 413 of FIG. 4A), a first electrode (e.g., the first electrode 441 of FIG. 4A) spaced apart from an inner surface of the through-hole, and movable within the through-hole, a part of the first electrode protruding to outside of the conductive frame, a second electrode (e.g., the second electrode 442 of FIG. 4A) disposed on the second surface, and contact with the part of the user's body when the electronic device is worn to the user, and a processor (e.g., the processor 550 of FIG. 5A); wherein the processor may be configured to, in response to identifying a designated event, identify whether the first electrode is electrically disconnected to the conductive frame; obtain an information about the user' body through the first electrode and the second electrode, based on identifying the first electrode is electrically disconnected to the conductive frame; and refrain from obtaining the information based on identifying the first electrode is electrically connected to the conductive frame.

According to an embodiment, the processor may be configured to identify that the first electrode is electrically connected to the conductive frame, based on identifying that an impedance value between the first electrode and the conductive frame is less than or equal to a reference value, and identify that the first electrode is electrically disconnected to the conductive frame, based on identifying that the impedance value exceeds the reference value.

According to an embodiment, the electronic device may further comprise an impedance measurement circuit (e.g., the impedance measurement circuit 520 of FIG. 5A) within the housing, and at least one switch (e.g., at least one switch 530 of FIG. 5A) within the housing, wherein, the processor may be configured to, in response to identifying the designated event, identify whether the first electrode is electrically disconnected to the conductive frame based on an impedance value between the first electrode and the conductive frame, by electrically connecting the impedance measurement circuit with the first electrode and the conductive frame via at least one switch, based on identifying the first electrode is electrically disconnected to the conductive frame, disconnect the conductive frame from the impedance circuit via at least one switch, and connect the impedance circuit with the first electrode and the second electrode via at least one switch.

According to an embodiment, the processor may obtain the information through the first electrode in contact with another part of the user's body and the second electrode in contact with the part of the user's body, based on identifying the first electrode is electrically connected to the conductive frame.

According to an embodiment, the designated event may include detecting the execution of software used for providing the information.

According to an embodiment, the designated event may include identifying the mode of the electronic device is changed from a first designated mode to a second designated mode.

According to an embodiment, the processor may be configured to provide a notification about whether the electronic device has submerged to the user, based on identifying the first electrode is electrically connected to the conductive frame.

According to an embodiment, the electronic device may further comprise an actuator disposed within the housing, wherein, the processor may be configured to vibrate the electronic device through the actuator (e.g., the actuator 540 of FIG. 5A) based on identifying the first electrode is electrically connected to the conductive frame.

According to an embodiment, the first electrode may extend from the inside of the housing along a direction perpendicular to a direction the first surface faces.

According to an embodiment, the electronic device may further comprise a sealing member (e.g., the sealing member 470 of FIG. 4A) sealing the through-hole by surrounding the first electrode.

According to an embodiment, the electronic device may further include a first non-conductive member (e.g., the first non-conductive member 461 in FIG. 4A) and a second non-conductive member (e.g., the second non-conductive member 462 in FIG. 4A) spaced apart from each other and coupled to the conductive frame to be in contact an inner surface of the through-hole and the first electrode.

According to an embodiment, an electronic device may comprise a housing (e.g., housing 410 in FIG. 4A) including a first surface (e.g., the first surface 410*a* of FIG. 4A), a second surface (e.g., the second surface 410*b* of FIG. 4A) facing the first surface and facing a part of the user's body when the electronic device (e.g., the electronic device 400 of FIG. 4A) is worn to the user, and a conductive frame disposed between the first surface and the second surface and including a first through-hole (e.g., the first through hole 413 of FIG. 4A), and a second through-hole (e.g., the second through hole 414 of FIG. 4A), a display (e.g., the display 420 of FIG. 4A) disposed on the first surface, a first electrode (e.g., the first electrode 441 of FIG. 4A) spaced apart from an inner surface of the first through-hole, and movable within the first through-hole and a part of the first electrode protruding to outside of the conductive frame, a second electrode (e.g., the second electrode 442 of FIG. 4A) disposed on the second surface, and contact with the part of the user's body when the electronic device is worn to the user, a third electrode (e.g., the third electrode 443 of FIG. 4A) spaced apart from an inner surface of the second through-hole, and movable within the second through-hole, and a part of the third electrode protruding to outside of the conductive frame, a fourth electrode (e.g., the fourth electrode 444 of FIG. 4A) disposed on the second surface spaced apart from the second electrode, and contact with the part of the user's body when the electronic device is worn to the user, and processor; wherein, the processor may be configured to, in response to identifying a designated event, identify whether the first electrode or the third electrode is electrically disconnected to the conductive frame; obtain an information about the user' body through the first electrode, the second electrode, the third electrode, and the fourth electrode, based on identifying the first electrode is electrically disconnected to the conductive frame and identifying the third electrode is electrically disconnected to the conductive frame; and refrain from obtaining the information, based on identifying the first electrode is electrically connected to the conductive frame or the third electrode is electrically connected to the conductive frame.

According to an embodiment, the processor may be configured to identify that the first electrode or the third electrode is electrically connected to the conductive frame, based on identifying that an impedance value between the first electrode and the conductive frame or the third electrode and the conductive frame is less than or equal to a reference value, and identify that the first electrode or the third electrode is electrically disconnected to the conductive frame, based on identifying that the impedance value exceeds the reference value.

According to an embodiment, the designated event may include detecting the execution of software used for providing the information.

According to an embodiment, the designated event may include identifying the mode of the electronic device is changed from a first designated mode to a second designated mode.

According to an embodiment, the processor may be configured to obtain the information through the first electrode, the second electrode, the third electrode, and the fourth electrode in contact with the different parts of the user's body, based on identifying the first electrode is electrically disconnected to the conductive frame and identifying the third electrode is electrically disconnected to the conductive frame.

According to an embodiment, the processor may be configured to provide a notification through the display to the user that the electronic device has been submerged, based on identifying the first electrode is electrically connected to the conductive frame or the third electrode is electrically connected to the conductive frame.

According to an embodiment, the electronic device may further include an actuator (e.g., the actuator 540 of FIG. 5A) disposed within the housing, wherein the processor may be configured to vibrate the electronic device through the actuator, based on identifying the first electrode or the third electrode is electrically connected to the conductive frame.

According to an embodiment, the electronic device may further include a first sealing member (e.g., the first sealing member 471 of FIG. 4A) sealing the first through-hole by surrounding the first electrode, and a second sealing member sealing the second through-hole by surrounding the third electrode.

According to an embodiment, the electronic device may further include a first non-conductive member (e.g., the first non-conductive member 461 of FIG. 4A) and a second non-conductive member spaced apart from each other and coupled to the conductive frame to be in contact an inner surface of the first through-hole and the first electrode, and a third non-conductive member (e.g., the second non-conductive member 462 of FIG. 4A) and a fourth non-conductive member spaced apart from each other and coupled to the conductive frame to be in contact an inner surface of the second through-hole and the third electrode.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., an internal memory 136 or an external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., a compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
  a housing including:
    a front surface,
    a rear surface, and
    a side surface including a conductive frame, the side surface positioned between the front surface and the rear surface;
  a first electrode spaced apart from the conductive frame and protruding to outside of the side surface;
  a second electrode disposed on the rear surface, and in contact with a part of a body of a user when the electronic device is worn on the user;
  impedance measurement circuitry;
  memory, in the housing, comprising one or more storage media storing instructions; and
  at least one processor in the housing, the at least one processor comprising processing circuitry,
  wherein the instructions that, when executed by the at least one processor individually or collectively, cause the electronic device to:
    obtain, through the first electrode, an electric signal,
    identify, using the impedance measurement circuitry, whether the first electrode is electrically disconnected from the conductive frame based on the electric signal,
    in response to identifying that the first electrode is electrically disconnected from the conductive frame, obtain biometric data about the body through the first electrode and the second electrode, and
    in response to identifying that the first electrode is electrically connected to the conductive frame, refrain from obtaining the biometric data about the body.

2. The electronic device of claim 1, wherein the instructions that, when executed by the at least one processor individually or collectively, further cause the electronic device to:
  identify an impedance value using the impedance measurement circuitry,
  identify that the first electrode is electrically connected to the conductive frame, based on identifying that the impedance value between the first electrode and the conductive frame is less than a reference value, and
  identify that the first electrode is electrically disconnected from the conductive frame, based on identifying that the impedance value exceeds the reference value.

3. The electronic device of claim 1, further comprising:
  at least one switch within the housing,
  wherein the impedance measurement circuitry is disposed in the housing; and
  wherein the instructions that, when executed by the at least one processor individually or collectively, further cause the electronic device to:
    identify whether the first electrode is electrically disconnected from the conductive frame based on an impedance value between the first electrode and the conductive frame, by electrically connecting the impedance measurement circuitry with the first electrode and the conductive frame via the at least one switch, and
    based on identifying the first electrode is electrically disconnected from the conductive frame, disconnect the conductive frame from the impedance measurement circuitry via the at least one switch, and connect the impedance measurement circuitry with the first electrode and the second electrode via the at least one switch.

4. The electronic device of claim 1, wherein the instructions that, when executed by the at least one processor individually or collectively, further cause the electronic device to obtain the biometric data through the first electrode in contact with another part of the body and the second electrode in contact with the part of the body, based on identifying that the first electrode is electrically connected to the conductive frame.

5. The electronic device of claim 1, wherein the instructions that, when executed by the at least one processor individually or collectively, further cause the electronic device to:
  identify an input requesting for obtaining the biometric data, and
  in response to identifying the input:

in case of identifying that the first electrode is electrically connected to the conductive frame, refrain from obtaining the biometric data, and in case of identifying that the first electrode is electrically disconnected from the conductive frame, obtain the biometric data.

6. The electronic device of claim 1, wherein the instructions that, when executed by the at least one processor individually or collectively, further cause the electronic device to:

provide a notification indicating that the electronic device has submerged, based on identifying that the first electrode is electrically connected to the conductive frame.

7. The electronic device of claim 1, further comprising:
an actuator disposed within the housing,
wherein the instructions that, when executed by the at least one processor individually or collectively, further cause the electronic device to:
vibrate the electronic device through the actuator based on identifying that the first electrode is electrically connected to the conductive frame.

8. The electronic device of claim 1, wherein the first electrode is protruded from an inside of the housing through a through-hole within the conductive frame.

9. The electronic device of claim 1, further comprising a first non-conductive member and a second non-conductive member spaced apart from each other and coupled to the conductive frame to be in contact with an inner surface of a through-hole and the first electrode.

10. The electronic device of claim 1, further comprising:
a third electrode, the third electrode electrically spaced apart from both the conductive frame and the first electrode; and
a fourth electrode disposed on the rear surface to be contacted with another portion of the body when the electronic device is worn by the user, the fourth electrode electrically spaced apart from the conductive frame,
wherein the instructions that, when executed by the at least one processor individually or collectively, cause the electronic device to:
in response to identifying a designated event, identify whether the first electrode or the third electrode is electrically disconnected from the conductive frame,
in response to identifying that the first electrode is electrically disconnected from the conductive frame and identifying that the third electrode is electrically disconnected from the conductive frame, obtain biometric data about the user through the first electrode, the second electrode, the third electrode, and the fourth electrode, and
in response to identifying that the first electrode is electrically connected to the conductive frame or the third electrode is electrically connected to the conductive frame, refrain from obtaining the biometric data about the user.

11. The electronic device of claim 1, wherein the conductive frame is configured to function as an antenna radiator.

12. The electronic device of claim 1, wherein the instructions that, when executed by the at least one processor individually or collectively, cause the electronic device to:
identify an impedance value using another electric signal obtained through the second electrode and the first electrode, identify whether the body is in contact with both the second electrode and the first electrode based on the impedance value, and
obtain biometric data about the user, using the another electric signal, based on identifying that the body is in contact with both the second electrode and the first electrode.

13. The electronic device of claim 5, wherein the instructions that, when executed by the at least one processor individually or collectively, further cause the electronic device to:
in response to identifying the input:
obtain, through the first electrode, the electric signal.

14. The electronic device of claim 5, wherein the instructions that, when executed by the at least one processor individually or collectively, cause the electronic device to:
identify detecting execution of software used for providing the biometric data as the input requesting for obtaining the biometric data.

15. The electronic device of claim 5, wherein the instructions that, when executed by the at least one processor individually or collectively, cause the electronic device to:
identify changing a mode of the electronic device from a first designated mode to a second designated mode as the input requesting for obtaining the biometric data.

16. The electronic device of claim 8, further comprising a sealing member sealing the through-hole by surrounding the first electrode.

17. The electronic device of claim 10, wherein the instructions that, when executed by the at least one processor individually or collectively, further cause the electronic device to:
identify that the first electrode or the third electrode is electrically connected to the conductive frame, based on identifying that an impedance value between the first electrode and the conductive frame or the third electrode and the conductive frame is less than a reference value, and
identify that the first electrode or the third electrode is electrically disconnected from the conductive frame, based on identifying that the impedance values between the first electrode and the conductive frame and between the third electrode and the conductive frame exceed the reference value.

18. The electronic device of claim 17, wherein the instructions that, when executed by the at least one processor individually or collectively, further cause the electronic device to:
obtain the biometric data through the first electrode, the second electrode, the third electrode, and the fourth electrode in contact with different portions of the body, based on identifying that the first electrode is electrically disconnected from the conductive frame and identifying the third electrode is electrically disconnected from the conductive frame.

19. The electronic device of claim 17,
wherein the first electrode is protruded from an inside of the housing through a through-hole within the conductive frame,
wherein the third electrode is protruded from an inside of the housing through another through-hole within the conductive frame, and
wherein the electronic device comprises:
a first sealing member sealing the through-hole by surrounding the first electrode; and
a second sealing member sealing the another through-hole by surrounding the third electrode.

20. The electronic device of claim 19, further comprising:
a first non-conductive member and a second non-conductive member spaced apart from each other and coupled to the conductive frame to be in contact with an inner surface of the through-hole and the first electrode; and
a third non-conductive member and a fourth non-conductive member spaced apart from each other and coupled to the conductive frame to be in contact with an inner surface of the another through-hole and the third electrode.

* * * * *